United States Patent
St Amant, III

(10) Patent No.: US 10,613,004 B1
(45) Date of Patent: Apr. 7, 2020

(54) WET GAS SAMPLE SYSTEM

(71) Applicant: Mayeaux Holding LLC, Gonzales, LA (US)

(72) Inventor: Valmond Joseph St Amant, III, St Amant, LA (US)

(73) Assignee: Mayeaux Holding, LLC, Gonzales, LA (US)

( * ) Notice: Subject to any disclaimer, the term of this patent is extended or adjusted under 35 U.S.C. 154(b) by 50 days.

(21) Appl. No.: 15/653,083

(22) Filed: Jul. 18, 2017

Related U.S. Application Data

(63) Continuation-in-part of application No. 15/615,772, filed on Jun. 6, 2017, now Pat. No. 10,436,678.

(51) Int. Cl.
*G01N 1/22* (2006.01)
*G01N 33/22* (2006.01)

(52) U.S. Cl.
CPC ......... *G01N 1/2247* (2013.01); *G01N 33/225* (2013.01)

(58) Field of Classification Search
CPC .. G01N 1/2035; G01N 1/22; G01N 2001/222; G01N 2001/2223; G01N 1/2247; G01N 2001/225; G01N 2001/2285; G01N 1/2205; G01N 1/44; G01N 30/04; F24H 1/102; F24H 3/02
USPC ............... 73/863.11, 863.12, 863.81–863.85, 73/864.01, 864.02, 864.21, 864.34, 73/864.72–864.74
See application file for complete search history.

(56) References Cited

U.S. PATENT DOCUMENTS

| | | | |
|---|---|---|---|
| 2,515,835 A | * | 7/1950 | Preston ..................... F17C 9/02 137/341 |
| 3,080,760 A | | 3/1963 | Piersma |
| 3,133,444 A | | 5/1964 | Karwat |

(Continued)

FOREIGN PATENT DOCUMENTS

CN          201043965 Y          4/2008

OTHER PUBLICATIONS

Abb Inc, Totalflow NGC8206 Chromatograph User's Manual, (C) 2009, Ver 2101510-002-rev.AE, US, See pp. 1-17, 2-25 & 2-58 thru 2-64.

(Continued)

*Primary Examiner* — Robert R Raevis
(74) *Attorney, Agent, or Firm* — Joseph T Regard, Ltd plc

(57) ABSTRACT

A system for on-stream sampling of pressurized process gas such as natural gas or the like, said system optimized for use with pressurized process gas having liquid entrained therein, or otherwise referenced as "wet". In the preferred embodiment, a probe and method of sampling is contemplated to provide linear sample of fluids from a predetermined of said fluid stream. Further taught is the method of preventing compositional disassociation of a gas sample having entrained liquid utilizing a probe having a passage formed to facilitate capillary action in fluid(s) passing therethrough. The present invention teaches a unique and innovative tube bundle with a separate power cord integrated therein to power a heated vaporizer, pressure regulator or other modular conditioning or other electrical component, the tube bundle of the present invention thereby dispensing with the need for a separate power cord, while providing higher capacity than prior art systems.

11 Claims, 21 Drawing Sheets

(56) References Cited

U.S. PATENT DOCUMENTS

| | | | |
|---|---|---|---|
| 4,086,922 A * | 5/1978 | Henderson | A61H 15/0092 601/19 |
| 4,100,806 A | 7/1978 | Barbonelle | |
| 4,283,947 A | 8/1981 | George | |
| 4,301,679 A | 11/1981 | Boyle | |
| 4,312,121 A | 1/1982 | Tweed | |
| 4,442,720 A | 4/1984 | Apley | |
| 4,537,071 A | 8/1985 | Waterman | |
| 4,625,570 A | 12/1986 | Witherspoon | |
| 4,688,537 A | 8/1987 | Calkins et al. | |
| 4,790,198 A | 12/1988 | Awtry | |
| 4,993,842 A * | 2/1991 | Morimoto | G01K 17/00 374/29 |
| 5,109,709 A | 5/1992 | Nimberger | |
| 5,154,087 A | 10/1992 | Wenshau | |
| 5,179,859 A | 1/1993 | Van Niekerk | |
| 5,237,878 A | 8/1993 | Hackenberg | |
| 5,440,941 A | 8/1995 | Kalidindi | |
| 5,501,080 A | 3/1996 | McManus et al. | |
| 5,521,130 A | 7/1996 | Welker | |
| 5,538,344 A | 7/1996 | Dybdahl | |
| 5,637,809 A | 6/1997 | Traina | |
| 5,834,657 A | 11/1998 | Clawson et al. | |
| 5,894,080 A | 4/1999 | Dybdahl | |
| 6,325,843 B1 | 12/2001 | Hickox | |
| 6,357,304 B1 | 3/2002 | Mayeaux | |
| 6,605,475 B1 | 8/2003 | Taylor | |
| 6,701,794 B2 | 3/2004 | Mayeaux | |
| 6,869,800 B2 | 3/2005 | Torgerson | |
| 6,904,816 B2 | 6/2005 | Mayeaux | |
| 7,004,041 B2 | 2/2006 | Mayeaux | |
| 7,134,318 B2 | 11/2006 | Mayeaux | |
| 7,162,933 B2 | 1/2007 | Thompson et al. | |
| 7,471,882 B2 | 12/2008 | Peebles et al. | |
| 7,717,000 B2 | 5/2010 | Xie | |
| 7,942,065 B2 | 5/2011 | Xie | |
| 7,958,794 B2 | 6/2011 | Sahibza et al. | |
| 8,196,480 B1 | 6/2012 | Mayeaux | |
| D674,052 S | 1/2013 | Thompson | |
| 8,522,630 B1 | 9/2013 | Mayeaux | |
| 9,200,986 B1 | 12/2015 | Mayeaux | |
| 9,257,027 B2 | 2/2016 | Williamson | |
| 9,395,280 B2 | 7/2016 | Thompson et al. | |
| 9,459,185 B2 | 10/2016 | Thompson et al. | |
| 9,535,427 B2 | 1/2017 | Patterson et al. | |
| 9,995,659 B1 | 6/2018 | Mayeaux | |
| 2006/0229528 A1 | 10/2006 | Heske | |
| 2007/0158469 A1 | 7/2007 | Burgener | |
| 2007/0164562 A1 | 7/2007 | Valaskovic | |
| 2007/0217960 A1 * | 9/2007 | Sekela | B01L 1/02 422/400 |
| 2009/0078442 A1 * | 3/2009 | Lin | H02G 3/088 174/50.51 |
| 2010/0145634 A1 | 6/2010 | Pinguet | |
| 2010/0212757 A1 | 8/2010 | Patterson | |
| 2010/0319468 A1 | 12/2010 | Peebles | |
| 2011/0036445 A1 | 2/2011 | Hall | |
| 2012/0033219 A1 | 2/2012 | Hokamura | |
| 2013/0052083 A1 * | 2/2013 | Kirby | F24H 1/142 422/70 |
| 2013/0220036 A1 | 8/2013 | Faust | |
| 2014/0041463 A1 | 2/2014 | Vethe | |

OTHER PUBLICATIONS

Federal Register, vol. 81, No. 222 BLM 43 CFR Parts 3175.111-112 "Onshore Oil and Gas Operations; Federal and Indian Oil and Gas . . . " Nov. 17, 2016, pp. 81578-81580 US.
Abb Inc, Portable NGC8206 Natural Gas Chromatograph DS_2101179, Copyright 2017, US.
A+ Corp LLC, Genie tm High Velocity Probe Product Sheet, PPS-SGP-HV-120803, Copyright 2003 US.
Valtronics Inc, Mustang Sampling Sample Conditioning System MSCS P53, MSB-P53 vol. 1.2 (C) 2009.
Valtronics, Inc Mustang Sampling Pony Heated Probe Encl PONY, MSB-PONYCS vol. 2.1 (C) 2009.
Welker, Sample Conditioning Heated System Manual, Model SCHS, Manual IOM-132, Rev C, Apr. 20, 2016 , p. 6.
Mustang Sampling LLC, MSCS Product Brochure, MSB-MSCS vol. 1.5, (C) 2009-2017.
Mustang Sampling LLC, Solar Powered Sample Conditioning System SPSCS Product Brochure MSB-PonySOL vol. 2.1 (C) 2014-2017.
Mustang Sampling LLC Sample Conditioning System P53 Product Brochure MSBC-P53-CE vol. 2.2 (C) 2009-2017.
Mustang Sampling LLC Pony Heated Probe Enclosure Product Brochure MSBC-C-PONYCS vol. 4.4 (C) 2009-2017.
A+ Corp LLC, Genie Heated Regulator GHR Product Sheet, SCC-GHR-PS_0906 (C) 2006.
A+ Corp, LLC, Genie, GHR Heated Regulator Product Sheet, SCC-GHR0PS_1116, (C) 2012.
A+ Corp, LLC, Genie GPHV General Purpose Probe Product Sheet, SCC-GPHV-PS_0116, (C) 2012.
A+ Corp, LLC, Genie Vaporizer Product Sheet, SCC-GV-PS_0106, (C) 2006.
A+ Corp , Genie 760 Direct Drive Probe Product Sheet, SCC-7600PS_0116, (C) 2012 US Dept Interior, BOL, Operator Letter (redacted), Jan. 19, 2017 regarding FMPs (Facility Measurement Points).
Matheson Gas, "The BTU Accuracy Connection to Profitability . . . ", 2 page brochure, 2010.
US Dept of Interior, BOL Operator Letter (redacted) Mailed Jan. 19, 2017, US.
Thermon Manuf Co, Brochure PAF00270714 "installing Non-Heated Wires within a Tube Bundle", Thermon Manuf Co, undated, US.
Mustang Sampling LLC, Mustang Intelligent Vaporizer Sampling System Model 2, Product Sheet, Mustang Sampling LLC, Ravenswood, WV, (C) 2009-2016, US.
Welker Inc, SCHS Sample Conditioning Heated System, Product Sheet, Welker, Inc, Sugar Land, TX (C) 2016, US.
McMaster-Carr Supply Co, Web Catalog at https://www.mcmaster.com/#catalog/123/1/=1ap8126, Stainless Steel Tubing, p. 143, downloaded Dec. 26, 2017, US.
Research Gate, discussion regarding capillary in Gas Chromatograph, printed Dec. 15, 2017 https://www.researchgate./net/post/What_is_a_capillary_column_ for_GC_and_how_does_it_work.
Acme Cryogenics, Acme Model CV Cryogenic Valve Brochure, 2013, US, Page 2.
Acme Cryogenics, Vacuum Insulated Pipe brochure, 2015, US.
Cryofab CFCL Series Vacuum Insulated Flexible hose leaflet, 2015, US.
Intertec, SL Blocktherm Self-Limiting Block Heater Product Sheet, HD-662ca, 2013.
Intertec, Diabox 87 Product Sheet, KD222-12en Diabox 87, 2017.
Thermon Manufacturing CO brochure form PAF0027-0714 Installing Non-Heated Wires Within a Tube BundleAug. 9, 2008.
McMaster-Carr Supply Co, Web Catalog, https://www.mcmaster.com/#catalog/123/153, Extreme-Presure Stainless Steel Tubing, 2016, p. 153,2016, US.
Raevis, R, USPTO, "Non-Final Rejection", U.S. Appl. No. 15/854,663 (CIP of 15653083), St Amant III Inventor, dated Jun. 28, 2019.
Ex Parte Quayle Action in U.S. Appl. No. 15/854,663, Mailed Oct. 9, 2019, 4 Pages.
"Non-Final Rejection" U.S. Appl. No. 15/615,786, St Amant III, Inventor, dated Sep. 23, 2019, 12 Pages.

* cited by examiner

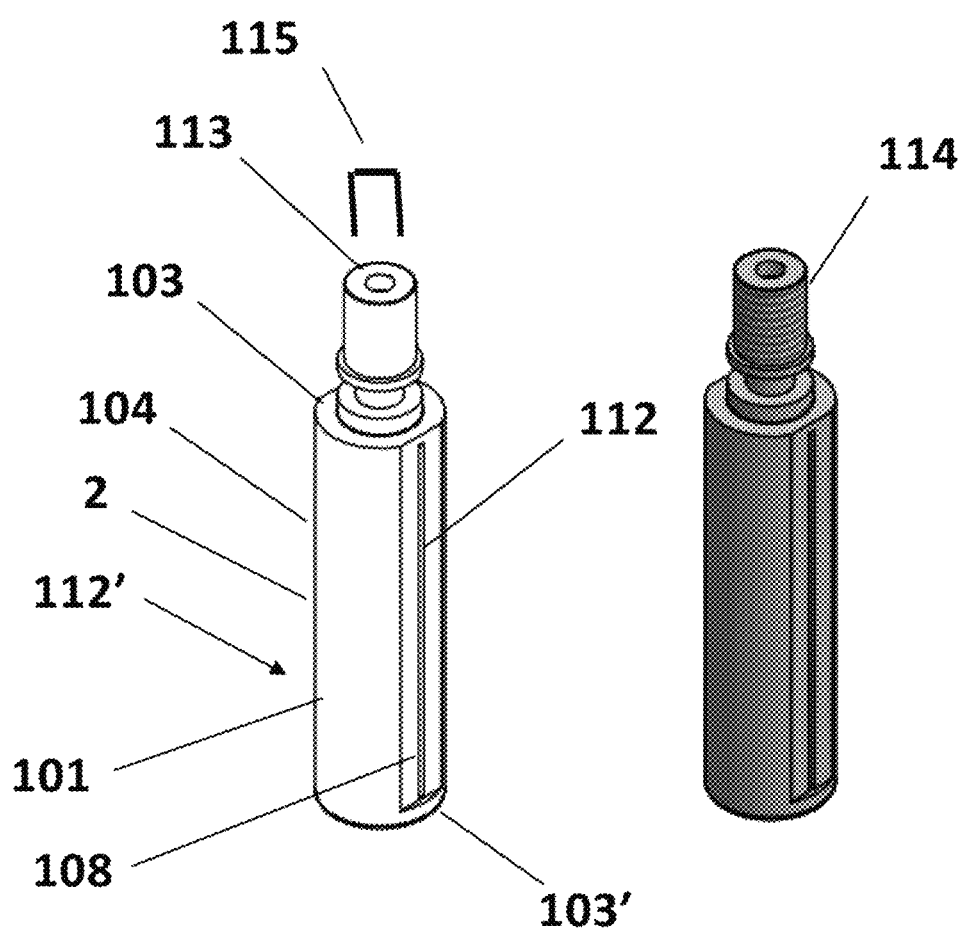

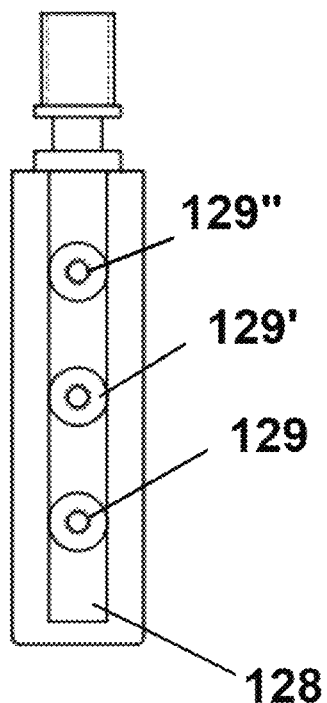
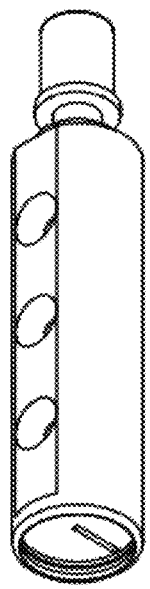
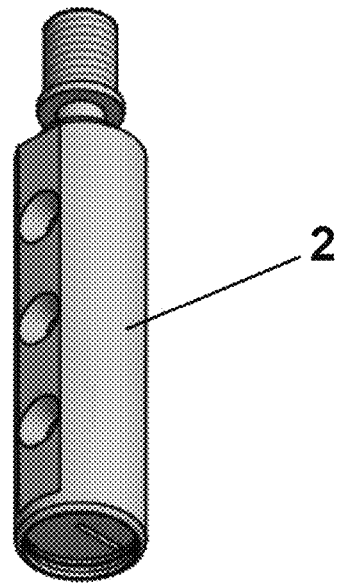
FIG 8A          FIG 8B          FIG 8C
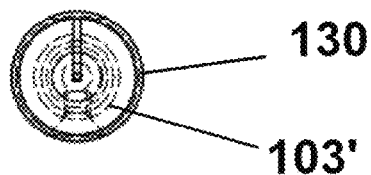
FIG 8D

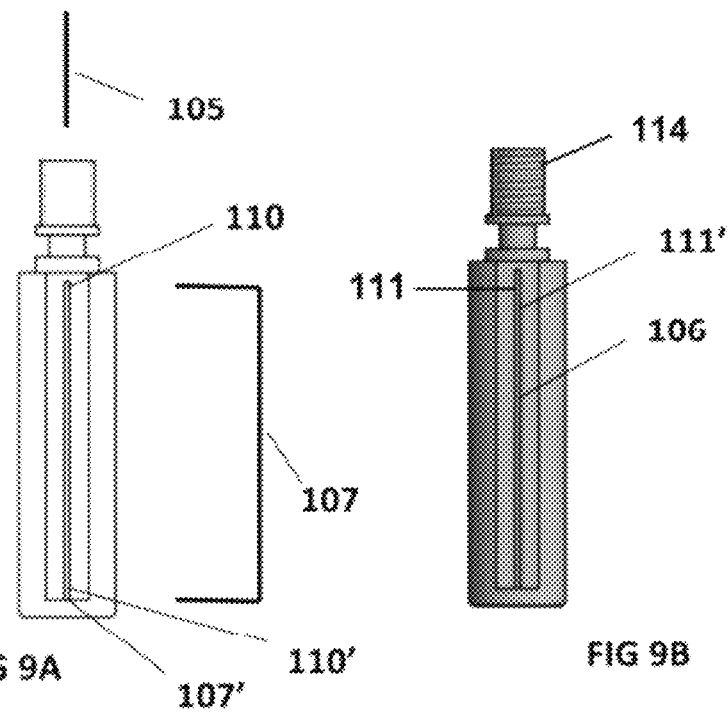
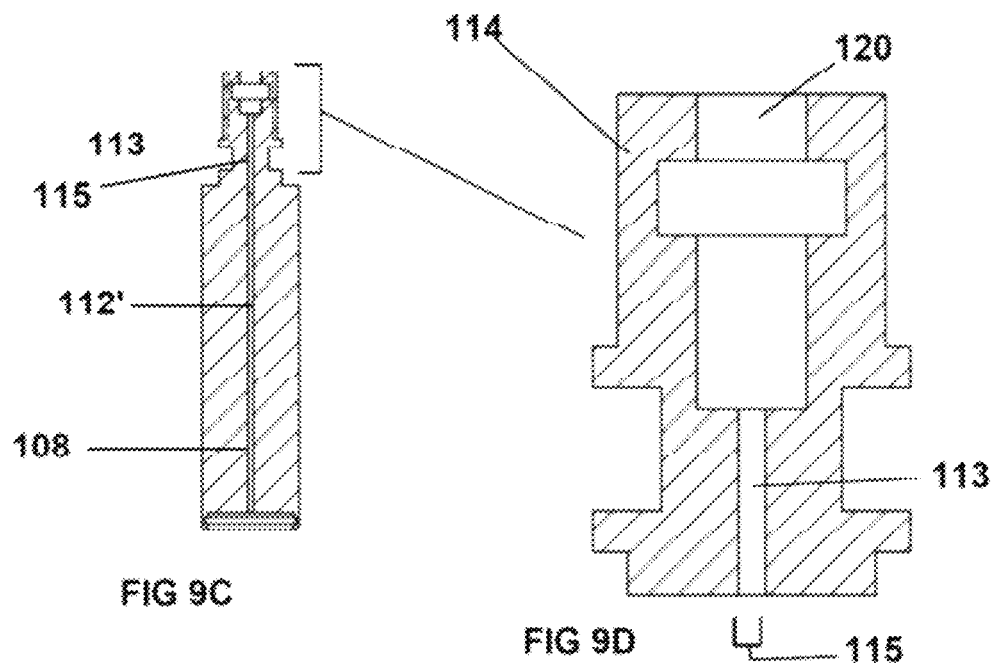

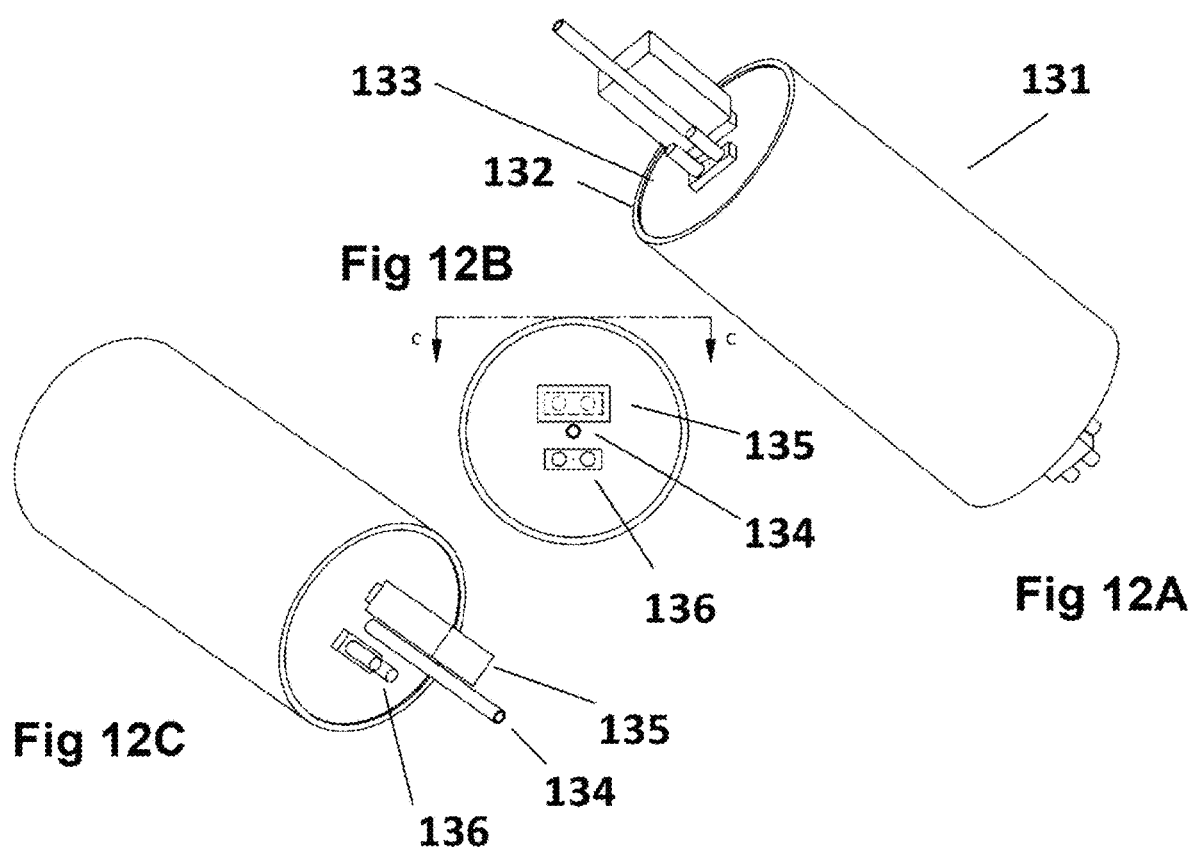

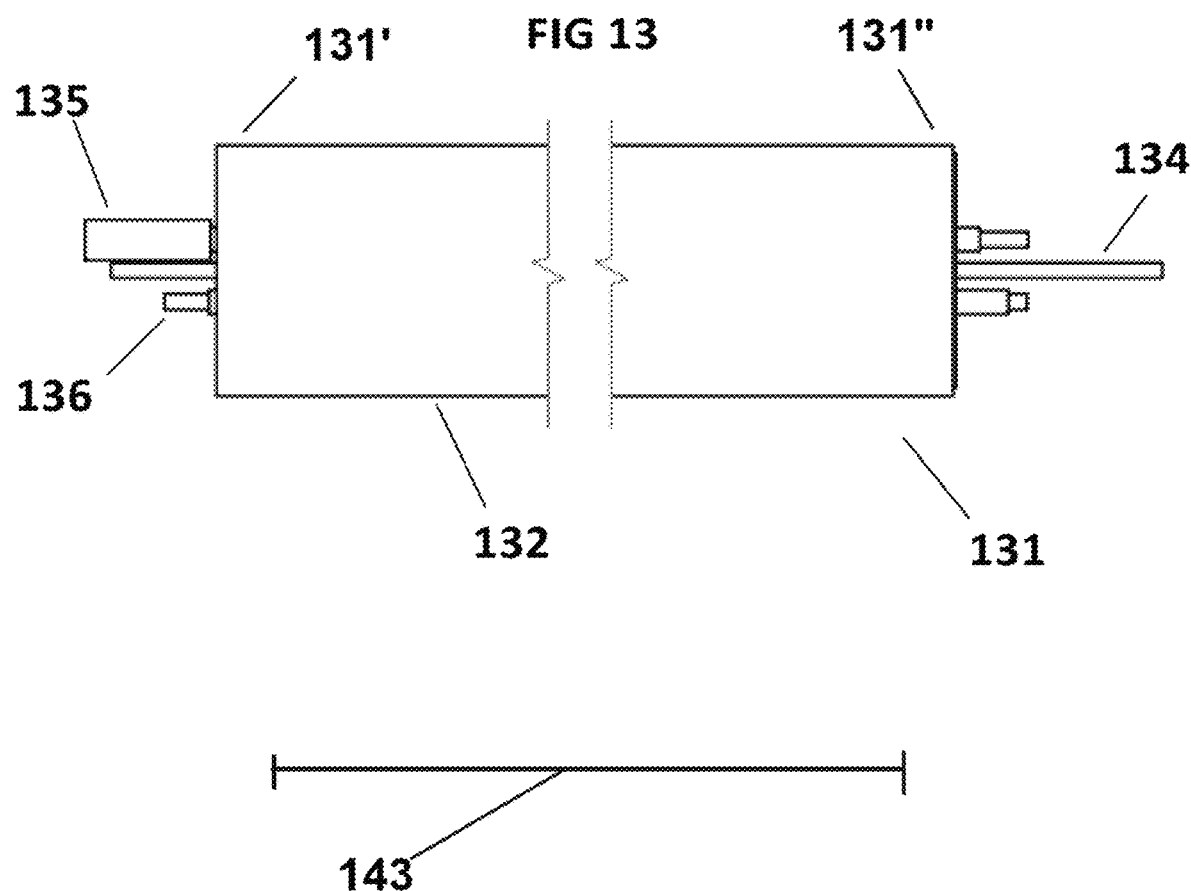

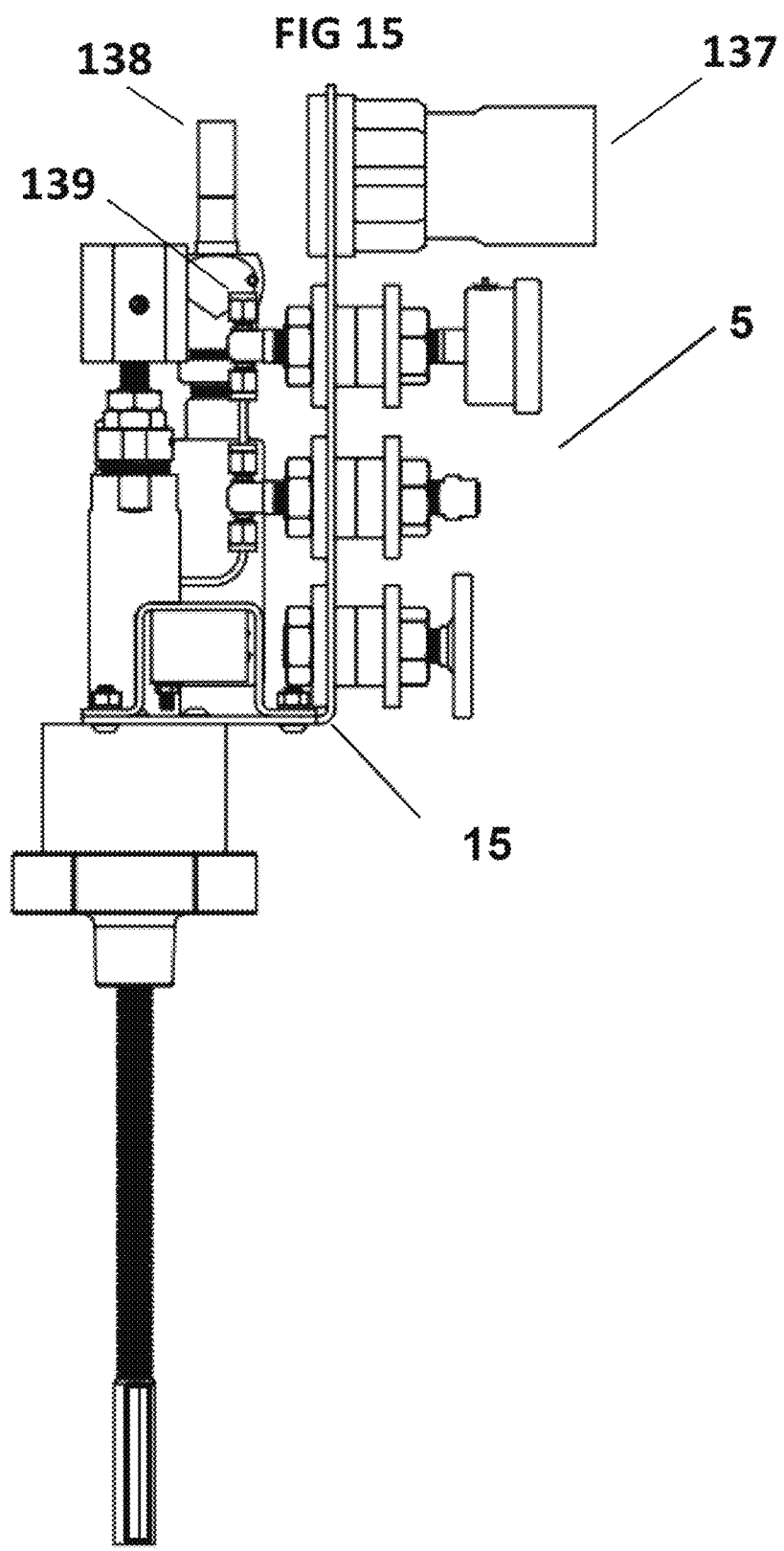

WET GAS SAMPLE SYSTEM

STATEMENT OF CONTINUING APPLICATION

The present application is a continuation-in-part of U.S. Utility patent application Ser. No. 15/615,772 filed Jun. 6, 2017 entitled WET GAS SAMPLE SYSTEM, listing Valmond Joseph St Amant, III as inventor.

FIELD OF THE INVENTION

The present invention relates to sampling of pressurized process fluids, and more particularly a system for on-stream and/or spot sampling of pressurized process gas having liquid entrained therein, otherwise known and referenced as multiphase or "wet" including but not limited to natural gas or the like. The present invention contemplates a unique and innovative probe formed to take a linear sample of fluids at a predetermined area of said fluid stream, including the center-third, in compliance with recent Bureau of Land Management (BLM) requirements, in combination with a tube bundle incorporating a separate power cord to power a heated vaporizer, pressure regulator or other modular conditioning/electrical component. The present invention provides a sampling system compliant with newly-revised BLM orders, and is particularly suitable for use in BLM regulated Facility Measurement Points (FMP).

BACKGROUND OF THE INVENTION

Natural Gas is comprised of a mixture of gases (See API 14.1 Section 6.3 and naturalgas.org). Natural gas is bought and sold based on its heating value (BTU), which is derived from a compositional analysis of the natural gas. It is the BTU content that determines the monetary value of a given volume of natural gas. This BTU value is generally expressed in decatherms (one million BTU).

To determine the total heat value of a given volume of gas, a sample of the gas is analyzed, and from the compositional data, its heat value per unit volume is calculated. This value is generally expressed in BTU/cu ft. The typical range of transmission quality gas ranges between 1000 and 1100 BTU/cu ft. Production gas, storage facility gas, NGL, and new-found Shale Gas can have much higher heating values up to or even exceeding 1500 BTU/cu ft.

There has been a long-standing controversy between gas producers and gas transporters regarding entrained liquid typically present in most high BTU/cu ft. gas (rich or "wet" gas). Transporter tariffs require essentially liquid-free gas. Liquid in the gas being transported causes operational and safety problems. The practice is to separate the liquid before entering a transport (pipe) line.

The API 14.1 standards (Manual of Petroleum Measurement Standards, 2006) scope does not include supercritical fluid (dense phase) or "wet gas" "(a term referenced by the Natural Gas industry as a gas that is at or below its hydrocarbon dew point temperature and/or contains entrained liquid), nor does the GPA 2166 standard (Obtaining Natural Gas Samples for Analysis by Gas Chromatography, 2005). In summary, there is no known standard which defines how to obtain a "representative sample" of a natural gas supply having entrained liquid in any form.

Therefore, to fully comply with the current industry standards, membrane-tipped probes such as the A+Corporation Genie Probe (see U.S. Pat. Nos. 6,357,304, 6,701,794, 6,904,816, 7,004,041, and 7,134,318) have been used for many years to shed entrained liquids inside pressurized pipelines. Electrically powered heaters may be provided, which are powered by a separate power line included in the tube bundle. This power line is separate from the heat trace. These heaters are used to prevent hydrocarbon gas condensation in liquid-free gas samples.

Companies such as Mustang Sampling, LLC have bolted enclosures to the A+Corporation membrane-tipped probes, and are believed to utilize third party, electrically-powered heater blocks and A+Corporation cartridge-type heated regulators for the enclosure, as well as third party electrical heat trace products. See for example U.S. Pat. No. 7,162, 933. See also U.S. Pat. No. 9,459,185 relating to a solar powered sample analyzing system. See also ABB NGC8206 User Manual, Copyright 2009, Pages 1-17 and 2-58 through 2-64, available for download at their website.

Other housing or enclosure providers include, for example, vendors such as Intertec Hess GmbH's instrumentation component offerings on the internet at www.Intertec.info. Intertec Hess is not only a provider of enclosures but is also a provider of the electrically-powered heater blocks. Splicing kits suitable for such an application may be found at Protherm Industries Inc website, which offers, for example, a FE Series Splice Kit which could be used in this application; splice kits also available from other third-party providers such as Pentair at their website.

Mustang Sampling, LLC Brochures MSB-PONY and MSB P53, available at their website, can include products incorporating A+Corporation Genie membrane tipped probes, and utilize third party, electrically-powered heater blocks and A+Corporation cartridge-type heated regulators and third-party heat trace, as described above. Mustang Sampling brochure MSB P53 illustrates a product which can include A+Corporation GENIE brand membrane separators (U.S. Pat. No. 7,555,964, a CIP of U.S. Pat. No. 7,097,693 (listing the present Inventor as second Inventor)) in an enclosure, which is ideally mounted in the vicinity of the analyzer, which may include additional electrically-powered heater blocks and electrically powered heated regulators (See Mayeaux U.S. Pat. No. 6,357,304, Thompson U.S. Pat. No. 7,162,933, and Thompson US 2012/0325694 A1).

Other companies, such as Welker Engineering, use non-membrane probes (fixed probes) and bring the liquids outside the pipeline to reject the liquids inside enclosures containing an electrically powered heated regulator and then returning the liquid back to the pipeline, while hanging a hinged enclosure onto the probe (see Welker SCHS manual, page 6, at their website, and U.S. Pat. No. 7,471,882). The purpose of these sample systems is to reject entrained liquids and maintain the sample system temperature above the sample dew point, to prevent further condensation.

The above and other known prior art rely upon power being readily available for electrical cartridge heater devices and electrical heater blocks, to provide heat for the sample systems to prevent condensation in liquid-free gas samples, not to vaporize liquids. Vacuum-jacketed tubing has also been used commercially for liquified natural gas sample systems for decades to insulate and preserve sample temperature. Vacuum jacketed tubing providers include companies like Acme Cryogenics and Cryofab. Also see Thompson U.S. Pat. No. 9,395,280 B2.

Recently the Bureau of Land Management (BLM) has revised 43 CFR 3175 (Order 5), The Onshore Oil and Gas Operations, Federal and Indian Oil and Gas Leases, Measurement of Gas effective Jan. 17, 2017, as indicated in the Federal Register, Vol 81, No 222, Sections 3175.111 and 3175.112, pages 81578-81580, issued 17 Nov. 2016.

Sections 3175.111 and 3175.112 now mandate a sampling protocol that is outside of the scope of API 14.1 and GPA 2166, by mandating sampling of two-phase samples (gas with entrained liquids) without rejecting the liquids, to provide a sample to the analyzer.

The above BLM order tries to reference parts of API 14.1 and GPA 2166, but is believed outside the scope of both of those industry standards. Further, said BLM order forbids the use of membranes, or any other type of filter and/or means of liquid rejection in the probes used to take the sample. Therefore, under this BLM order as it presently stands, it appears that contaminants like glycols and amines cannot be rejected, filtered, or removed from the sample that is taken from the pipeline. In addition, the present BLM order requires liquids and gases to be removed from the center-third of the pipeline, as well as heated sample lines to vaporize any liquids removed before they reach the analyzer.

Some of the sample points under the above referenced BLM order are in Facility Measurement Point (FMP) areas having electrical power availability. The power available may be 110V AC at high volume FMP sites, or 24V DC at low volume FMP sites. The 24V DC available may be from solar power. Solar power has been traditionally used in natural gas sampling for decades, for example see U.S. Pat. No. 5,501,080A to McManus et al, claiming a 1994 Priority date, as one example as well as Thompson U.S. Pat. No. 9,459,185, and vendors such as ABB (See the ABB NGC8206 user manual pages 1-17 and 2-58 through 2-64, copyright 2009, available at the company website).

Under the above referenced BLM order, these BLM sample points will be required to not just heat the sample to prevent condensation of liquid-free gas, but to also vaporize the entrained liquids removed with the gas samples. The BLM regulated locations with low volume FMPs may utilize portable low power gas analyzers that are powered from the technician's vehicle instead of on-site stationary conventionally powered gas analyzers such as gas chromatographs or other types of gas analyzers.

GENERAL SUMMARY DISCUSSION OF THE INVENTION

The present invention is configured to provide a single-phase gas sample to the analyzer without rejecting the liquids, the present system designed to be compliant with and particularly suitable for use in BLM regulated FMP areas, providing a unique sample system which is compliant with new BLM order 5, and without the problems and shortcomings associated with the prior art sample systems referenced above.

The present invention does not require the use of membrane filters or any other filter or method that would reject liquids. The present system contemplates a unique probe formed to take a linear sample of fluids at the medial area of said fluid stream, including the center-third, when required. The unique design and method of operation makes it particularly suitable for BLM order 5, providing compliant sample probes and methodologies. The present invention is also uniquely designed to not just provide heat to prevent condensation in liquid-free gas samples, but to also vaporize the multiphase sample utilizing a separate power cord in the tubing bundle.

Unlike the above discussed, prior art sampling systems, the present invention teaches a new and innovative "integral slice" sampling process, wherein a very thin slice of the total volume of the source fluid flowing through a conduit or pipeline is captured by a streamlined container arrangement suspended in said source fluid, in a similar manner to an integral in calculus—a limiting procedure which approximates the area of a curvilinear region by breaking the region into thin vertical slices—with nominal flow disturbance, and in which trapped fluid is subsequently withdrawn and isolated in a location outside of the source fluid flowing stream.

Further, unlike dynamic isokinetic techniques, the system of the present invention insures that the representative sample taken either in spot, batch or continuous fashion is not allowed to disassociate due to the very small internal cavity of the slot and outflow passage following the slot. Empirical testing verifies that, if the diameter of the passage is sufficiently small, then the combination of surface tension (which is caused by cohesion within the liquid and adhesive forces between the liquid and container wall) and the higher velocity sweep will act to propel the liquid as well as the gas through the passage, preventing disassociation. The pipeline area is very large compared to the probe's very small interior, and because of this vast difference, fluid in the probe will always be of a higher velocity than the pipeline fluid.

The high gas velocity (higher than the source velocity of the pipeline) of the very small internal cavity would then sweep all of the liquid particles at least at the same velocity as the gas particles being transported from the source to the probe. Therefore, it would remain "associated" with the gas from which it condensed. Small particles such as that which comprise smoke are known to behave somewhat like large molecules. High velocity gas in the small internal diameter bore of the probe will prevent any significant layer of liquid from accumulating on the surfaces. Even if an ultra-thin layer were to coat the probe's interior, the total area is so small that the impact would be negligible.

The present invention provides a far superior sampling solution for wet gas streams, including high HC dew point gases, which traditionally have been difficult to sample dynamically, due to phase changes and resulting composition changes which can be triggered by flow, pressure, and/or temperature.

The present invention thereby provides a unique sample system designed to solve the problems of prior art sample systems, while complying with the new BLM order 5.

The inlet of the present invention features a capillary outflow passage following the linear-slot probe. The capillary outflow passage may be in the form of a passage formed in the probe or capillary tubing inserted therein. In either case, the passage is formed to facilitate capillary action or motion, at higher velocity in "wet gas" flowing therethrough, to prevent the two-phase sample from disassociating as it is transported to any modular conditioning components, for example, heated pressure reducing regulator(s) and/or vaporizer(s).

As discussed above, prior art systems that were designed to reject or remove liquids from the gas sample utilized electricity to power electrical devices such as heater blocks. Similarly, prior art systems utilized electricity to power heated regulators to prevent condensation in liquid-free samples due to JT cooling associated with pressure reduction of a gas or cold ambient environments, that could cool the sample below its hydrocarbon (HC) dew point.

However, the additional electrical power required to not just overcome JT cooling due to the pressure reduction in liquid-free gas samples or to offset ambient temperatures but to now vaporize liquids in BLM regulated FMP sites adds additional electrical load that must now also overcome the latent heat of vaporization. Such an additional load may surpass the limited available power coming from the heat trace, which traditionally was tapped for relatively low power electrical needs.

Rather than relying on power from the heat trace, the present invention provides a separate power cord in a customized, tube bundle for utilization as the power source. The power cord may bring 11V AC or 24V DC to the modular sample system utilizing the tube bundle. The power cord may be connected to vaporizers, regulators, or other powered modular components of the two-phase sample system, for example. The regulator may be a single-stage or multistage regulator, such as, for example, assignee's patent number U.S. Pat. No. 8,220,479. An economic advantage to utilizing a power cord provided in the tube bundle is gained by eliminating the need for the long runs of conduit, and multiple conduit fittings.

With the above discussed innovations, the present invention provides a novel and unique modular conditioner/sampling system which, unlike the prior art, is not designed to specifically reject entrained liquids, instead utilizing vaporization to provide a single-phase sample via the unique tube bundle power configuration. Accordingly, unlike prior art systems, the present system is designed to be fully compliant with BLM order 5 Facility Measurement Points (FMP).

To prevent sample distortion after the probe, the capillary passage with associated higher velocity following the linear-slot sampling probe of the present invention does not allow the two-phased sample to disassociate before it is vaporized by the uniquely passive heated pressure reducing regulator. These components are located inside a unique housing/enclosure that facilitates 100% access to all components. The present housing/enclosure accomplishes this objective without hinges or diagonal cuts. The system is designed so that the enclosure is independent of the probe and the components. The enclosure can be easily and completely removed without disturbing the probe or any other components of the system, while protecting the components and decreasing heat loss.

BRIEF DESCRIPTION OF DRAWINGS

For a further understanding of the nature and objects of the present invention, reference should be had to the following detailed description, taken in conjunction with the accompanying drawings, in which like parts are given like reference numerals, and wherein:

FIG. 7A is an isometric, front view of the probe tip of FIGS. 5-6B, illustrating the linear slot formed along the length of the body and threaded connection end with capillary passage.

FIG. 7B is a greyscale view of the probe tip of FIG. 7A.

FIG. 8A is a rear view of an embodiment of the probe tip of FIG. 7A, illustrating a series of tapped holes or screws situated in spaced relationship along the length of the rear of the probe tip, for holding an optional screen filter sized to prevent solid particulates from entering the slot.

FIG. 8B is a perspective view of the invention of FIG. 8A, illustrating the position of the forward sampling slot in relation to the tapped holes.

FIG. 8C is a greyscale view of the invention of FIG. 8B.

FIG. 8D is a bottom, partially cutaway view of the invention of FIG. 8A.

FIG. 9A is a close-up, frontal view of the invention of FIG. 7A.

FIG. 9B is a greyscale view of the invention of FIG. 9A.

FIG. 9C is a side, partially cut-away, partially cross-sectional view of the invention of FIG. 9A.

FIG. 9D is a side, partially cut-away, partially cross sectional, detailed view of the threaded end of probe tip 114 and outflow passage 113 of FIG. 9C.

FIG. 10 C is a cross-sectional, close-up, side view of the receiver formed to receive the capillary tube in the threaded area of the slotted probe tip.

FIG. 12A is a first side, perspective view of a tube bundle configuration 131 with cover 132 and insulation 133 as utilized in the preferred embodiment of the tube bundle interface for heated regulator of the present invention.

FIG. 12B is an end view of the tube bundle configuration with cover and insulation of FIG. 12A.

FIG. 12C is a second side, perspective view of the tube bundle configuration with cover of FIG. 12A.

FIG. 13 is a side view of the invention of FIG. 12A illustrating a length of tube bundle showing a terminated end 135 and components including sample tube 134 and power cord 136.

FIG. 15 is a side view of the modular sample system of an exemplary embodiment of the present invention, illustrating a tube bundle boot 137 installed on the bracket of the system.

DETAILED DISCUSSION OF THE INVENTION

Preferably, the sample conditioning system of the present invention (FIGS. 1-20) is mounted at the source of the sample, in this case a pipeline having pressurized process gas.

Figure 1:
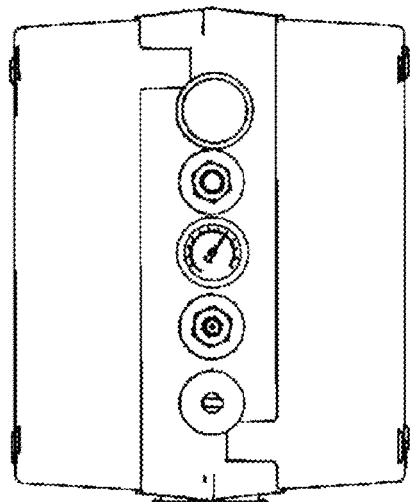
FIG. 1 is a frontal view of a sample modular sample conditioning system comprising modular sampling and/or conditioning components mounted to a substrate bracket, enclosed via a housing/enclosure.
Figure 2:
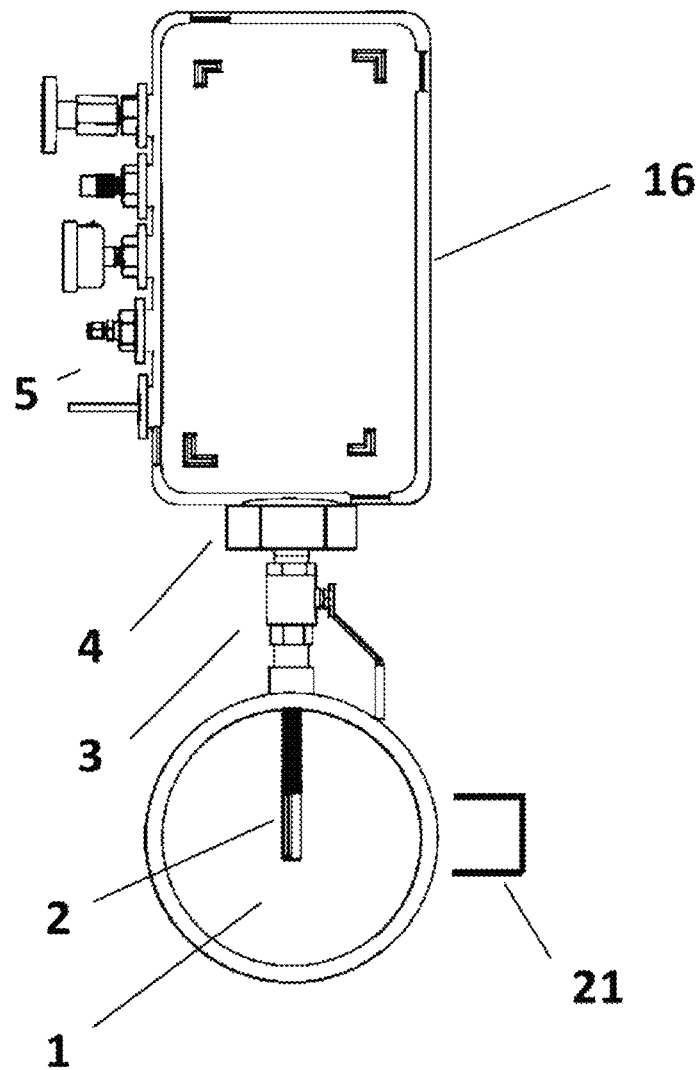
FIG. 2 is a side view of the invention of FIG. 1, further showing an end view of the source of gas with entrained liquids, a linear sampling probe of the present invention situated therein, providing a passage to the modular sampling/conditioning components via substrate coupling 4.
Figure 3:
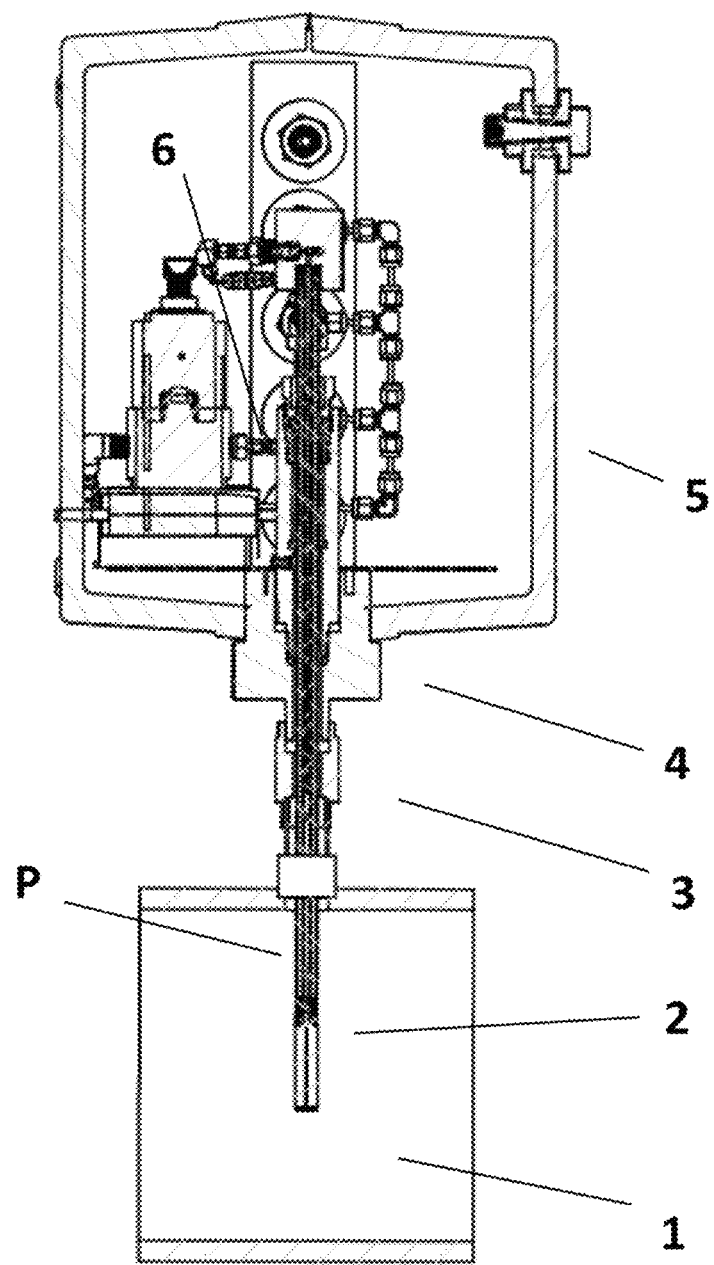
FIG. 3 is a rear, partially-cut-away view of the invention of FIGS. 1-2, illustrating the linear sampling probe of the present invention, the substrate coupling to prevent the disassociated collection of gas having entrained liquids therein.

Referring to FIGS. 1-2, substrate coupling 4 is provided to provide a base for connection of the process flow to the modular sample system 5. The substrate coupling is mounted to the process isolation valve 3. The coupling 4 connects the process source 1 to the modular sample conditioning system of the present invention. Enclosure 16 is engaged to and supported by the substrate coupling 4, and is provided to house and protect the modular components (as further discussed herein). FIG. 3 is a cutaway view of FIGS. 1-2.

Linear Sample Probe and Method of Sampling

Figure 4:
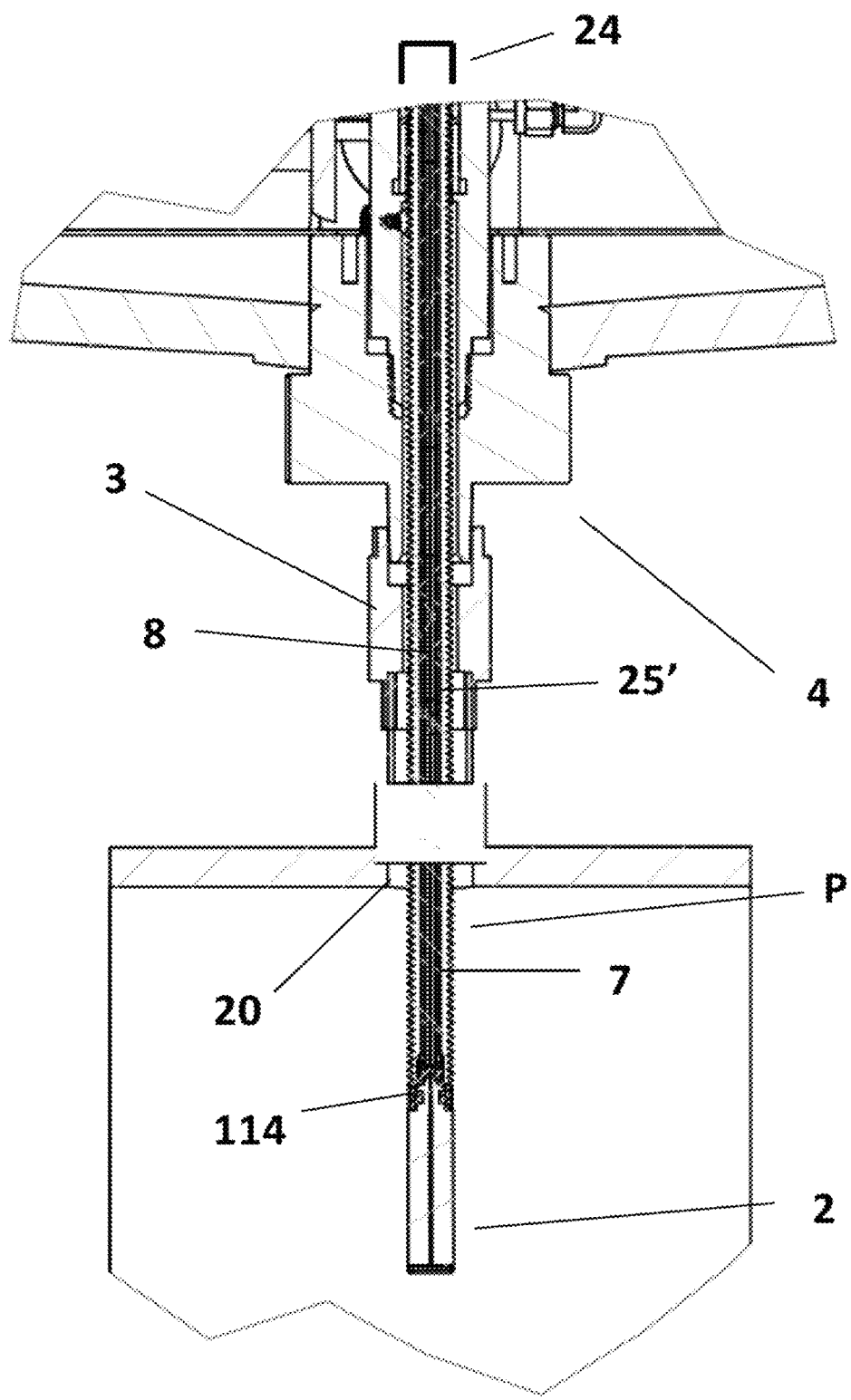
FIG. 4 is partial, close-up view of the probe and substrate FIG. 3.
Figure 5:
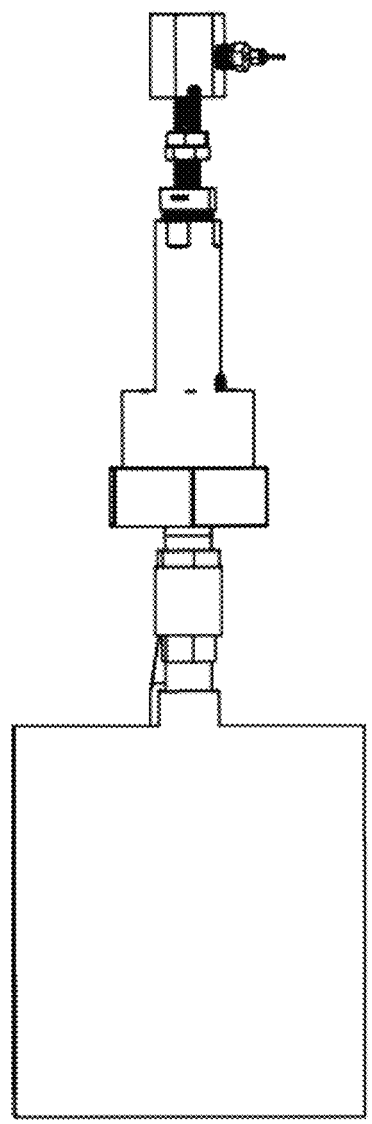
FIG. 5 is a side view of a pipeline containing a process gas flow having a linear sampling probe mounted thereto to sample the contents therein.
Figure 6A:
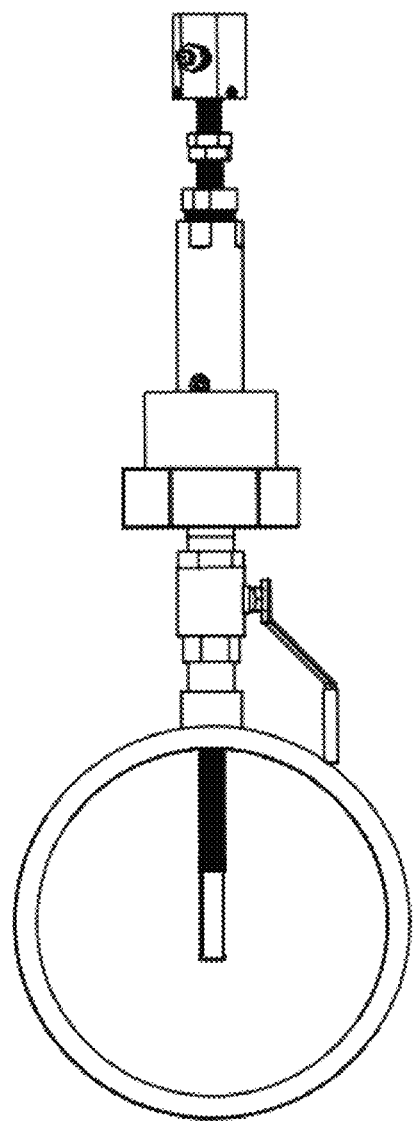
FIG. 6A is an end view of FIG. 5 showing the linear sampling probe with probe tip positioned at the center-third, medial area of the pipeline, so as to provide a center-third, medial sampling of same.
Figure 6B:
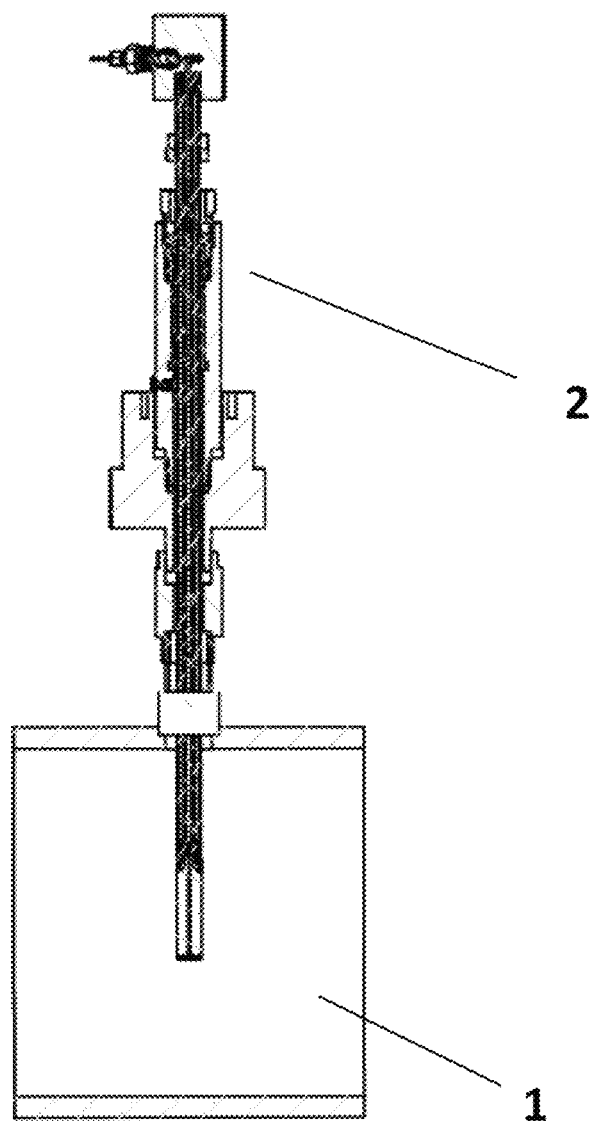
FIG. 6B is a side, sectional, cut-away view of FIG. 5 showing the insertion mechanism supporting the probe tip.
Figure 10:
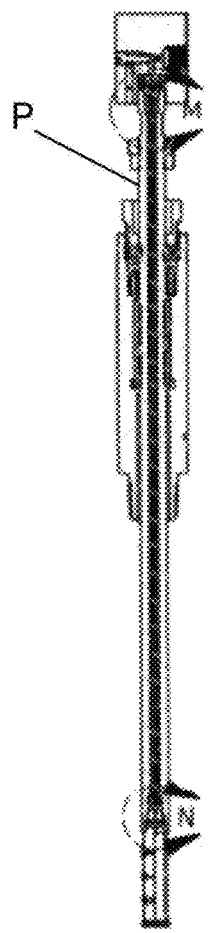
FIG. 10 illustrates a side, partially cut-away, partially cross-sectional view of the probe with slotted probe tip of the present invention having the capillary line through the length of the probe via probe passage, passing through the probe first end, rack, and the second end to probe tip.
Figure 10A:
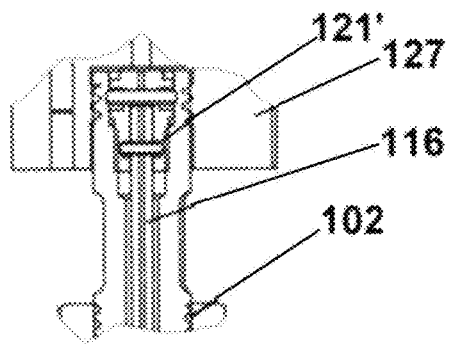
FIG. 10A is a side, partially cut-away, detailed view of the first end of the capillary tube engaging a flow component for flow out of the probe, sealed via O-Ring.
Figure 10B:
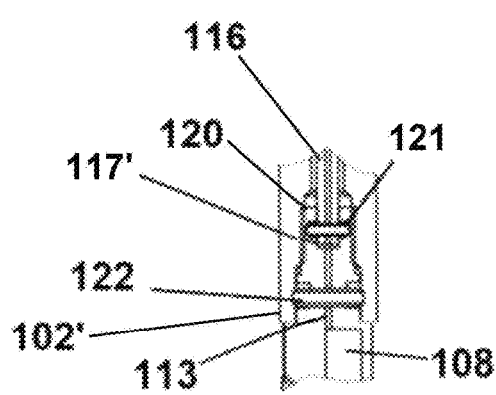
FIG. 10B is a side, partially cut-away, detailed view of the second end of the capillary tube engaging a receiver formed within the threaded area of the slotted probe tip of the present invention, via sealed O-rings.
Figure 10C:
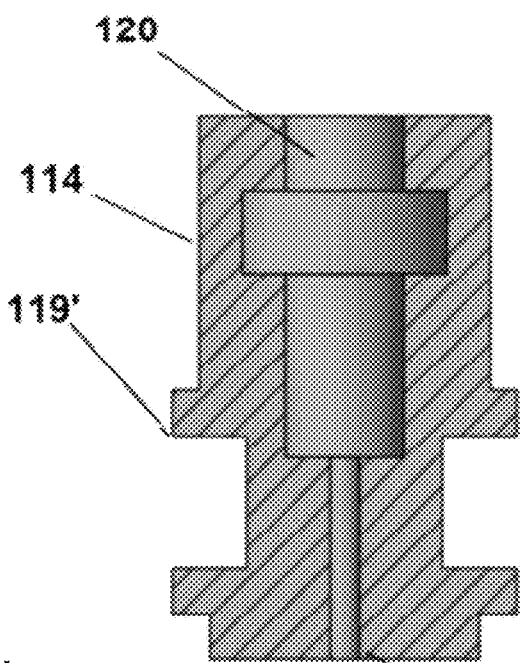
FIG. 10D is a side frontal, partially cut-away, partially cross-sectional view of the probe with slotted probe tip of FIG. 10.
FIG. 10E is a side frontal view of the probe tip of the present invention, illustrating the capillary tube aligned for insertion therein (the capillary tube will be positioned to pass through the probe to the probe tip as will be discussed herein).
Figures 10D, 10E:
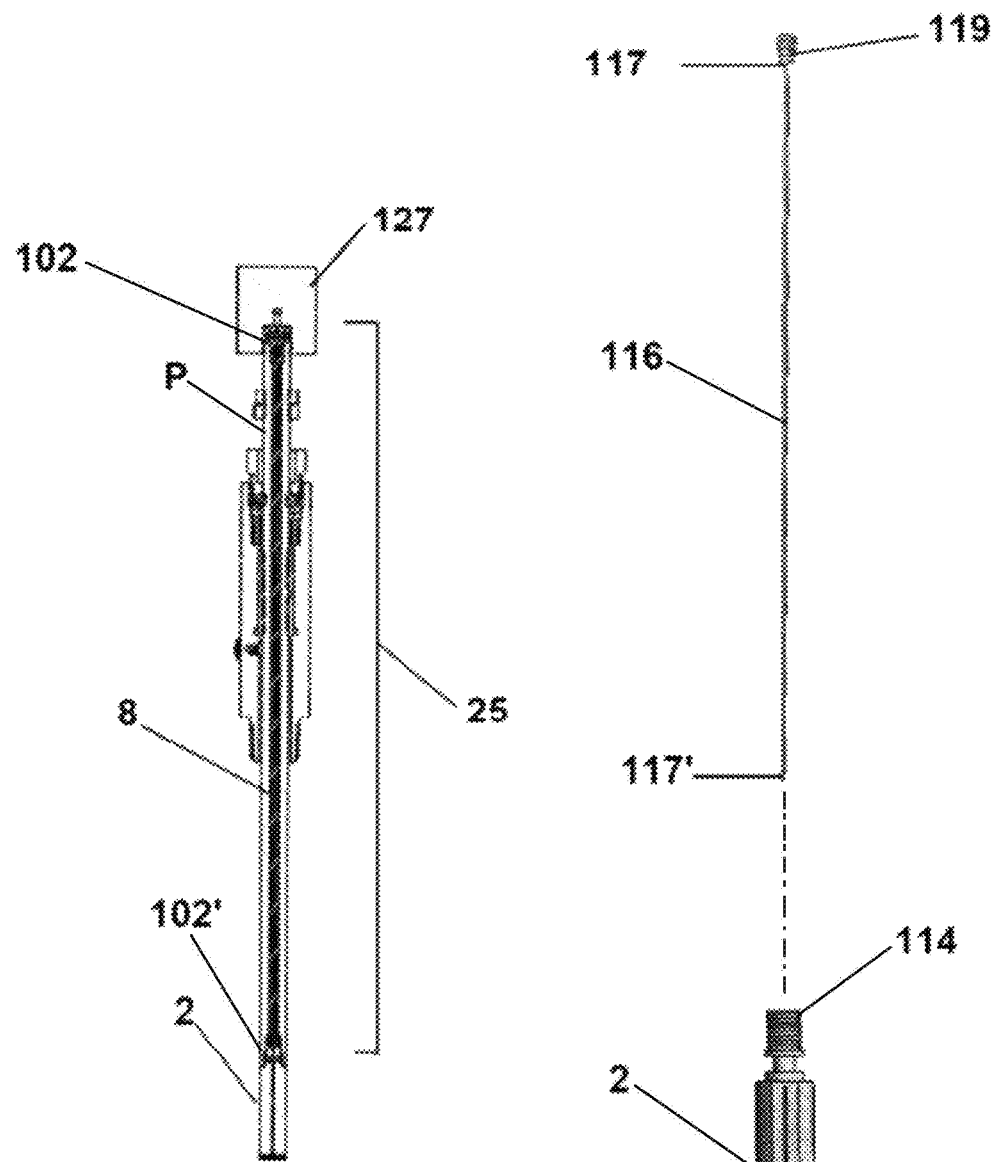

FIGS. 1-3 show pressurized source of gas (a/k/a process source) with entrained liquids 1 with the linear, slotted sampling probe tip 2 positioned in the fluid stream so that the collection slot faces the fluid flow, the probe tip shown position in the center-third area to sample the center-third 21, medial area of the flow stream, although the probe length and associated collection area can be modified as required. As shown, a probe isolation valve 3 is provided to selectively open and close the flow from the probe to the modular sample conditioning system 5, as required. As shown, the probe P, has a length 25 and first 102 and second ends 102', as will be further discussed herein. For insertion, a rack 25' may be provided along the probe P length as shown in FIG. 4.

Referring to FIGS. 7A-10E, formed through the outer wall 104 of body 101 of linear sampling probe tip 2 is an elongated, continuous or uninterrupted opening 106 having a length 107 aligned with the longitudinal axis 105 of the body 101, the opening 106 having a relatively narrow width 107', and ends 110, 110' to form a slot 108 penetrating the outer wall or surface of the body, the slot forming first 11 and second 111' side walls within the body forming an outer edge 112 and an inner edge 112' corresponding to its depth and providing a passage to outflow passage 113 having a small inside diameter as shown.

In the preferred embodiment of the invention shown in the figures, the slot 108 preferably has a relatively uniform width 107' preferably corresponding to, or less than, that of opening 106, while providing passage about to the longitudinal 105 body 101 at the innermost edge 112' of the slot, about halfway through body 101. The slot as shown runs along longitudinal axis 105, although the length and position of the slot can vary depending upon the application.

As shown, the slot 108 in the exemplary, preferred embodiment of the probe tip of the present invention runs from just below the first 103 end of body 101 to about the second end 103' of body 101, with the inner edge 112' of the slot 108 engaging outflow passage 113 having a small inside diameter 115, as shown, which is formed to engage, as required, (FIG. 3) insertion probe P to provide a channel of flow of fluid therefrom, the outflow passage 113 in the present embodiment preferably having an inner diameter 115 preferably equal to or less than the width 107' of slot.

The present system is formed to collect via the slot in the slotted probe tip a "linear sample" spanning a pre-determined area for sampling of the pipe, in the preferred embodiment of the present invention, the center-third area of the flow as is illustrated in FIG. 1-6B, or (in other versions) alternatively other zones or even the full span of the pipe from side-wall to side-wall, providing a representative sample of the fluid stream wherein a fluid sample of the fluid stream is collected along a line spanning the inner diameter of said pipe, even where there is present entrained liquid particles and even flowing liquid droplets/streams along the lower and/or upper surfaces of the pipe. While the present figures illustrate the position of the probe tip as vertical, this is not intended to be limiting, as the probe can be oriented at any angle relative the pipe, as long as the probe interface (insertion point) allows it.

The slot and outflow passage are preferably relatively narrow (less than $\frac{1}{32}$" depending on the volume of fluid being sample, the speed, viscosity, and other factors) to remove a very thin slice of the total breadth of the fluid stream, so as to provide an accurate composite of the total fluid flow using principals similar to the integral principle as used in calculus.

As described, the body 101 has first 103 and second 103' ends defining a length 107 therebetween, with a slot 108 defining a narrow opening to a centrally disposed outflow passage 113 of preferably equal or less diameter than the slot width, thus providing the "integral slice" (in the present example, less than $\frac{1}{32}$" wide slot from the outer surface of the probe) to intersect the small ID outflow passage (less than $\frac{1}{32}$"), so that process fluid having sample gas containing entrained liquid therein passes into the slot then is urged through the outflow passage to the probe at an equal or higher velocity than the fluid stream, so as to preserve the composition of the fluid stream and prevent disassociation of same.

Continuing with FIGS. 1-10, the threaded end 114 of slotted probe tip 2 threadingly engages the second end 102' of probe P. Probe P has a passage 8 formed therethrough along its length, the probe P having an outer diameter 24 formed allow its length to pass through probe isolation valve 3 (while in an open position) for selective insertion of the probe tip through 8 isolation valve 3, and into the fluid stream in pipe via passage 20.

The probe has formed therethrough along its length a probe passage 8 to provide for the passage of fluid from the probe tip 2 there through. In the preferred embodiment of the present invention, a capillary tube 116 (in the present embodiment, formed of stainless steel) is provided having a length and first 117 and second ends 117' and is situated through the length of probe passage 8, the second end 117' of capillary tube 116 formed to engage the outflow passage 113 of probe tip 2 at a receiver 120 formed within the threaded area 114 of probe tip 2, the first end 117' of capillary tube 116 sealingly engaging the probe tip's outflow passage 113 via first o-ring 121. The second end 102' of insertion probe P engages the probe tip 2 via o-ring 122 at retainer 119', providing sealed connection.

The capillary tube 116 in the present embodiment passes through the length of probe passage 8, the o-ring 121' at first end 117 of capillary tube engaging a flow component 127 (in this case, a 90 degree angle connector), and is sealed via o-rings and positioned to align with a capillary flow passage for flow to the conditioning components downstream, in the present case, the flow would run from capillary tube to regulator inlet 6, where any entrained liquid in the flow is vaporized by a heated regulator or vaporizer.

The capillary tube 116, like the probe tip 2 has an ID formed to facilitate capillary tube capillary flow properties in the fluid flowing therethrough, which, in the present case, for wet gas (natural gas having entrained liquid) has been found to exist in a passage having an inner diameter of less than $\frac{1}{32}$", although this figure could vary depending upon the surface tension of the liquids and other factors, further, the geometry of the capillary tube passage facilitate the flow of fluid therethrough at least at the velocity of the fluid stream from which the sample is taken, or at a higher velocity thereto.

In the present exemplary embodiment of the invention, the capillary tube 116 comprises Dursan $\frac{1}{8}$" OD stainless steel tubing, which is situated inside the probe passage (and rack), and the present tubing having a 0.030" or less ID to prevent sample disassociation via capillary action (and maintaining or providing enhanced fluid velocity), the optimal diameter of which can vary significantly depending upon the operational criteria and "wet gas" composition.

In the system of the present invention, it is imperative that no disassociation takes place in the sample fluid flow, from the moment the sampling occurs at the slotted probe tip, through the length of probe P (in the preferred embodiment, via capillary tube 116), to regulator inlet 6 (where the sample is conditioned via heated regulator and vaporized).

In the alternative to a capillary tube 116, the inner diameter (ID) of probe passage 8 itself could have an ID formed to maintain or increase flow velocity from the probe tip along its length, and accordingly have an ID equal to or less than the width of the opening forming the slot 108 in the slotted probe tip 2 or ID of the outflow passage 113 (i.e., less than $\frac{1}{32}$"), the geometry formed to provide capillary action in the wet gas flowing therethrough to prevent disassociation thereof.

Continuing with FIGS. 8A-9D, the slotted probe tip 2 of the present invention can include on the back side 128 opposite slot opening 106 threaded apertures 129, 129', 129" formed to threadingly receive screws or other fasteners to facilitate the attachment of a cylindrical solids filter screen 130 (for example, 40×40 mesh, 0.010" wire), to envelope the outer diameter (OD) of the probe tip and prevent solids from entering the opening 106 to slot 108, but large enough for the velocity of the sample to keep fluids from accumulating. A bottom screen disc may also be provided at the second end 103' of slotted probe tip 2 held in place with a spiral retaining ring.

The system of the present invention ensures that the representative sample taken either in spot, batch or continuous fashion is not allowed to disassociate by providing the very small internal cavity forming the outflow passage, to maintain or enhance the fluid flow velocity through the system. The pipeline area is very large compared to the probe's very small interior and because of this vast difference, fluid in the outflow passage from the slotted probe tip to the probe will always be flowing at a higher velocity than the pipeline fluid.

The high gas velocity (higher than the source velocity of the pipeline) of the very small internal cavity/fluid outflow passage is formed to sweep all of the liquid particles at the same velocity as the gas particles being transported from the source to the probe. Therefore, it would remain "associated" with the gas from which it condensed, as verified from Applicant's own empirical testing. High velocity gas in the small internal diameter bore forming outflow passage engaging the relatively narrow slot of the probe will prevent any significant layer of liquid from accumulating on the surfaces. Even if an ultra-thin layer were to coat the probe's interior, the total area is anticipated to be small that the impact would be expected to be negligible.

Continuing with the figures, as shown, the slotted probe tip 2 of the preferred embodiment of the present invention is engaged to the capillary tube (when utilized) then the end of an insertion probe P then is lowered or inserted (e.g., via the rack in the preferred embodiment) into a pipeline positioned in the medial or center-third area 21 of the pipe with the opening 106 forming the entrance of the slot 108 facing the flow stream. While the present illustration shows the sampling position of the probe such that the probe tip 2 is in the center-third area 21 for BLM compliance, it is noted that the probe tip can be positioned elsewhere as required.

A portion of the fluid stream comprising a "linear slice" of the fluid flow in the positioned portion of the pipe then passes into the opening, into and through the slot, then through the pressure of the flow stream is urged through the outflow passage, capillary tube with capillary flow on to the modular conditioning components for heating and/or collection, online analysis, monitoring, or other usage. As earlier indicated outflow passage in the preferred embodiment as well as downstream the probe tip to the conditioning components preferably has an inner diameter commensurate with the width of the slot formed in the body forming the slotted probe tip, resulting lesser area than the slot, so as to facilitate at least equal but more likely greater fluid velocity flow through said outflow passage, to keep the fluid from slowing and possibly disassociating.

Along with the higher velocity sweeping the wet gas sample so that it does not disassociate, conventional science recognizes that, as the inside diameter or cross sectional area of a slot or passage decreases, a static liquid having sufficient surface tension will interact with the walls of sufficiently small slot or passage to trigger static capillary functionality, a phenomenon known to occur when the static liquids adhesion to the walls is stronger than the cohesive forces between the liquid's molecules. Such a phenomenon, in combination with the higher velocity sweep, is believed to be an inherently motivating feature in the present invention when wet natural gas passes through the slot or wall when the clearance is at most (depending on various factor) equal or preferably generally less than 1/32", although the exact threshold where static capillary function can and will occur in this dynamic sweeping combination can vary depending on the composition of the wet gas, as well as other factors.

In the preferred embodiment of the present invention, the sample, once taken, is then directed to a heated conditioning component(s) to vaporize any liquids, providing a single-phase sample, then to a process analyzer, monitor, sample container, or other end use.

Considering the above and foregoing, a method of sampling a wet gas from a fluid stream the present invention could therefore comprise the steps of, for example:
- a. providing a probe having a probe passage formed along its length having an inner diameter having a geometry to facilitate capillary action in wet gas flowing therethrough, at a higher velocity than said fluid stream;
- b. allowing wet gas to flow from said fluid stream into and through said probe so as to provide capillary action at the higher velocity;
- c. allowing said capillary action to prevent disassociation of said composition of said wet gas as it flows through said probe passage.

Still further, the method of sampling a wet gas comprising gas with entrained liquid in a fluid stream of the present invention could comprise, for example, comprising the steps of:
- a) providing a probe tip 2 engaging probe P, said probe tip comprising an elongated slot situated along its length;
- b) laterally positioning said probe tip in the fluid stream so that said slot faces the stream;
- c) utilizing said slot to receive a linear sample of flow of said stream into said body, providing received flow;
- d) flowing said received flow through a passage sized to have capillary flow properties to prevent disassociation; and vaporizing said received flow to provide a representative sample.

As discussed, to be compliant with present BLM regulations at FMPs, preferably the probe tip 2 would be situated in the center third (medial area) of the flow.

While less than 1/32" is indicated as an example of the diameter for capillary flow in the present wet gas application, it is reiterated that the optimal specific geometry can vary depending on a number of criteria. A combination of phase diagram data and empirical testing could be used as a guide to determine the optimum capillary diameter/geometry for the particular wet gas composition, taking further into account the particular pipeline/flow property/application/environmental and other factors.

Heat Trace Interface for Modular Conditioning Components

FIGS. 12A-19 illustrate applicant's preferred embodiment of a tube bundle interface wherein there is provided a unique power cord configuration in a customized tube bundle, to provide power to electrical components including the unique, modular conditioning system of the present invention, as will be further discussed, infra.

Heat Trace Interface for Heated Regulator

Figure 11:
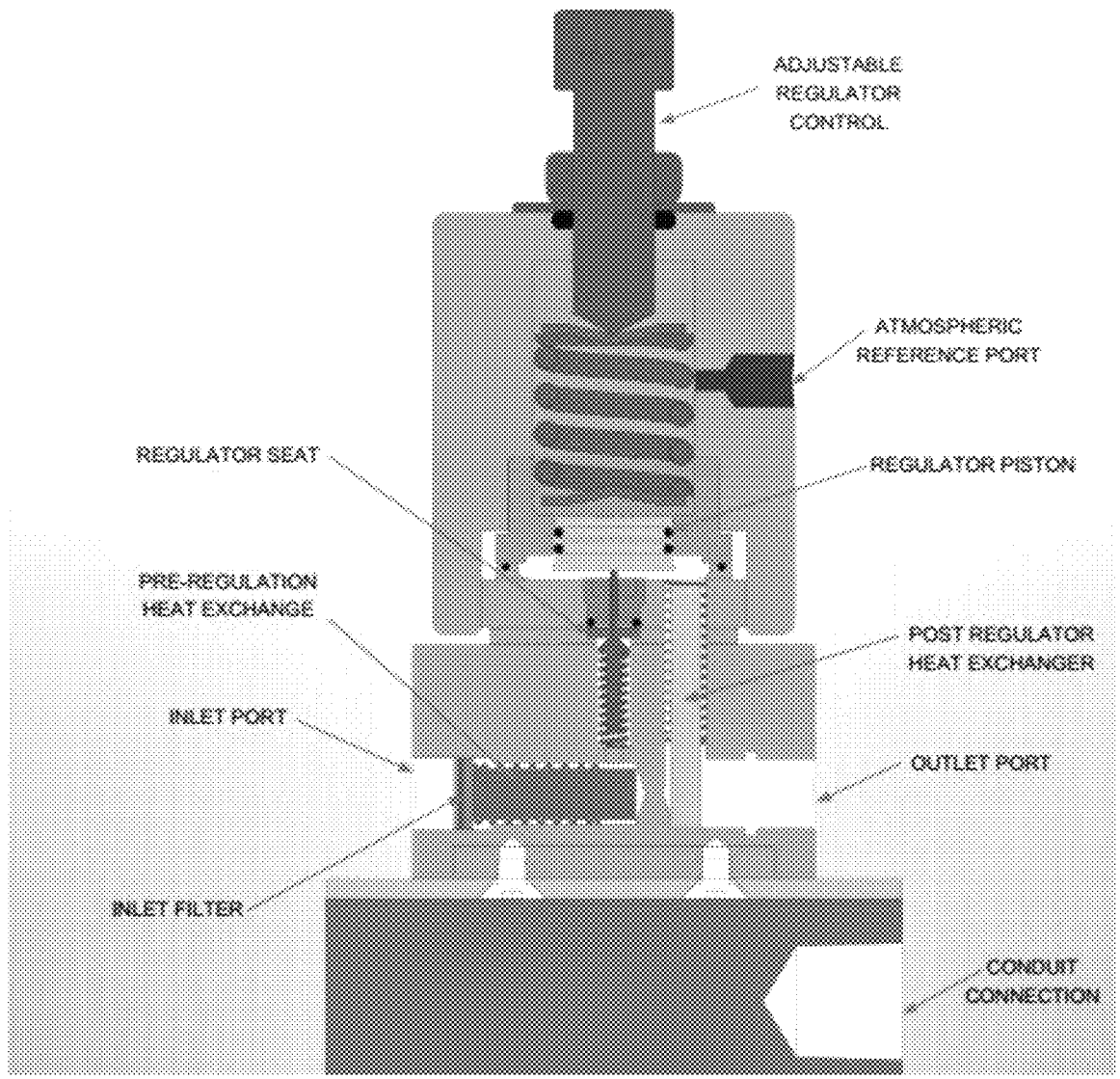
FIG. 11 is a side, partially cutaway view of the A+GENIE brand heated regulator first commercialized in 2004 and as such comprises Applicant prior art, with pre- and post-heat exchange features, and which requires an external source of electrical power.
Figures 14A, 14B:
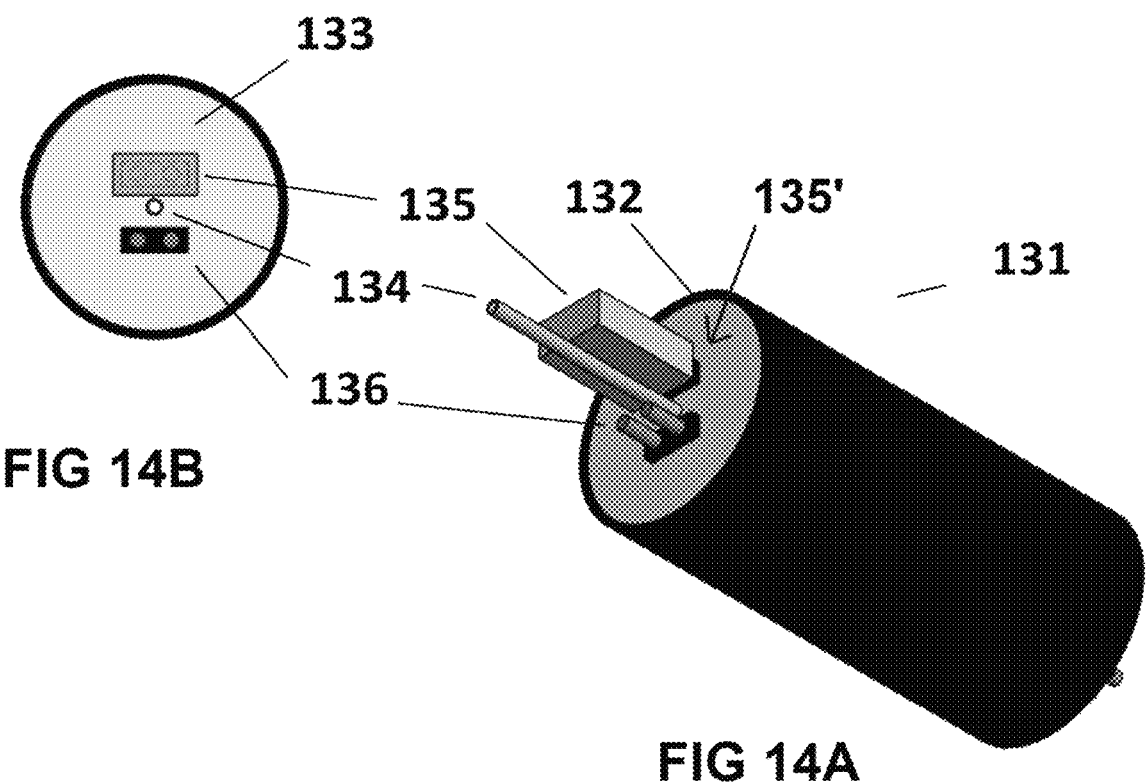
FIG. 14A is a perspective view of the tube bundle configuration of FIG. 12A in greyscale.
FIG. 14B is an end view of the invention of FIG. 12B, in greyscale.

The first embodiment of the tube bundle interface is configured to power to a heated regulator, such as applicant's Genie Heated Regulator (GHR) with pre-regulation heat exchange, and post regulator heat exchange, first commercialized in 2004, a design that requires electrical power, as shown in FIG. 11.

Figure 20:
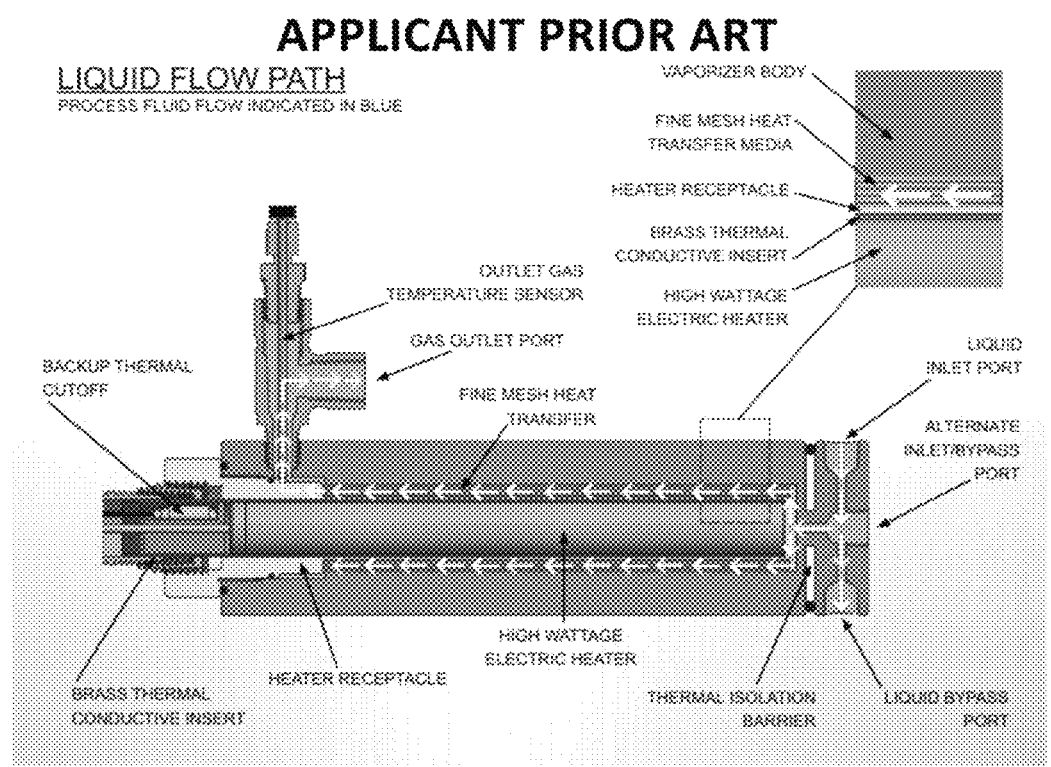
FIG. 20 is a side, partially cross-sectional, partially cutaway view of an exemplary A+GENIE brand vaporizer shown utilizing an electric heater (Applicant Prior Art) which may be modified for use in an alternative embodiment of the present invention.

FIG. 20 shows the applicant's Genie Vaporizer (GV) with brass thermal conductive insert commercialized in 2004, a design that requires electrical power, and which may also be powered via the tube bundle interface with integrated power cord of the present invention.

FIGS. 12A-14B show the power conductor or cord 136 of the present invention integrated into the tube bundle 131. Companies such as Thermon Manufacturing Company, www.thermon.com, offer custom tubing bundle options for their products, which might include non-heated auxiliary conductors within tube bundle, as denoted in their Application Flyer PAF0027-0714 (form PAF0027-0714).

FIG. 12 shows the tube bundle 131 having a length 143 and first 131' and second 131" ends, the tube bundle being protected along its length via cover 132, and having insulation 133 therethrough to isolate the components as desired. Situated along the length 143 of the tube bundle is sample tube 134 for conveying sample fluid from the modular sample conditioning system, the sample tube in the present preferred embodiment comprising a 1/8" OD Stainless Steel tube that is heated by an adjacent heat trace 135' along the length 143 of the tube bundle 131, the heat trace 135' terminating in terminated end 135 at the first end 131' of tube bundle 131.

In the present invention, a separate, non-heated power cord 136 of adequate gauge to convey the total required power to the unique sample conditioning system or other apparatus (for the length required) is provided in the tube bundle 131.

FIG. 13 shows that the length 143 of tube bundle 131 can vary depending on the power source location and the sample system location. FIG. 14 is a grayscale drawing of FIG. 12. Rather than using power from the heat trace which normally would provide inadequate power for vaporizers or the like, the present invention provides the separate power conductor or cord 136 in the tube bundle for utilization as the power source. The power cord 136 may bring 110V AC or 24V DC to the modular sample system utilizing the tube bundle, and again, its gauge may vary depending on its length and power requirements of the system.

Figure 16:
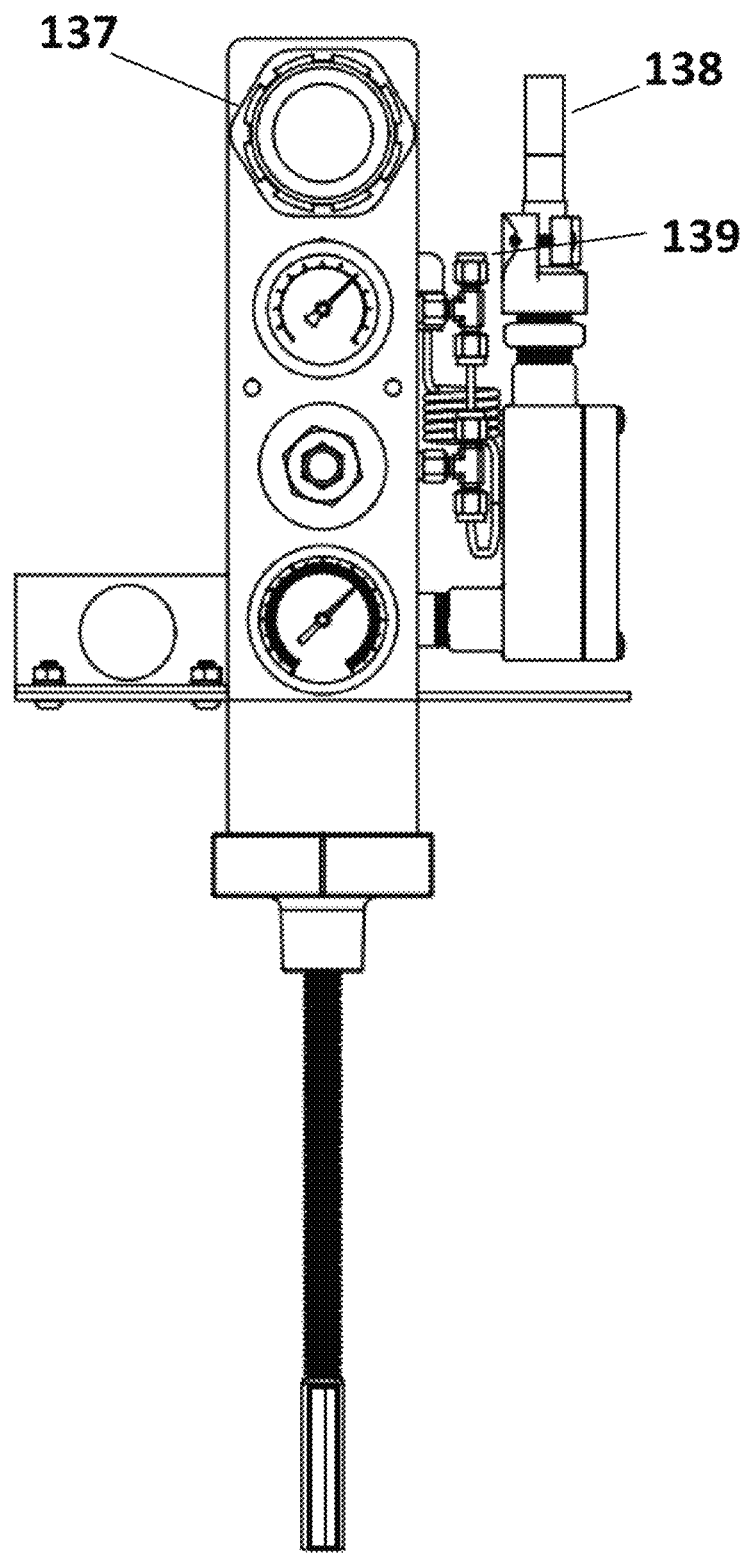
FIG. 16 is a front view of the invention of FIG. 15.
Figure 17:
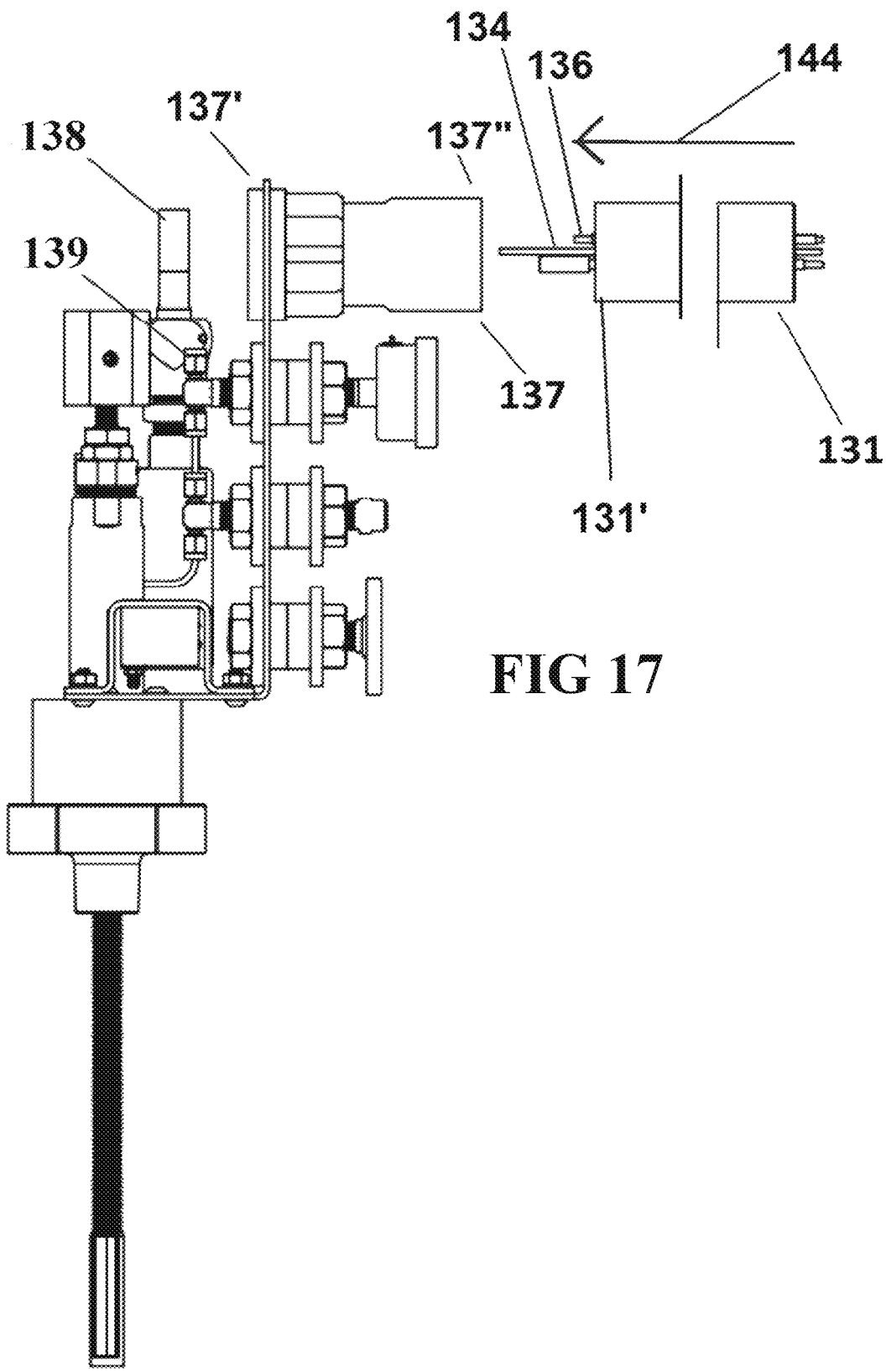
FIG. 17 is a side view of the invention of FIG. 15, further illustrating the insertion of the first end 131' of tube bundle 131 into tube bundle boot 137.

FIGS. 15-17 illustrate a tube bundle boot 137 having first 137' and second 137" ends, the first 137' end mounted to the bracket 15 of the modular sample system 5, the second end 137" end of tube bundle boot 137 formed to receive the first end 131' of tube bundle. In addition, the first 137' end of tube bundle boot 137 is formed to allow power cord 136 to pass therethrough to engage power cord receiver 138, or visa-versa.

The sample tube 134 in tube bundle 131 is formed to pass from the second end 137' of tube bundle boot 137 and engage in sealed fashion and connect to outlet tubing connection 139 (referencing FIG. 14).

Continuing with FIGS. 16-17, tube bundle 131 end is inserted into and slidingly engages tube bundle boot 137 and is swaged in place. Power cord 136 then is inserted into and slidingly engages power cord receiver 138, providing power to component wire associated with the conduit portion of power cord receiver 138.

Figure 18:
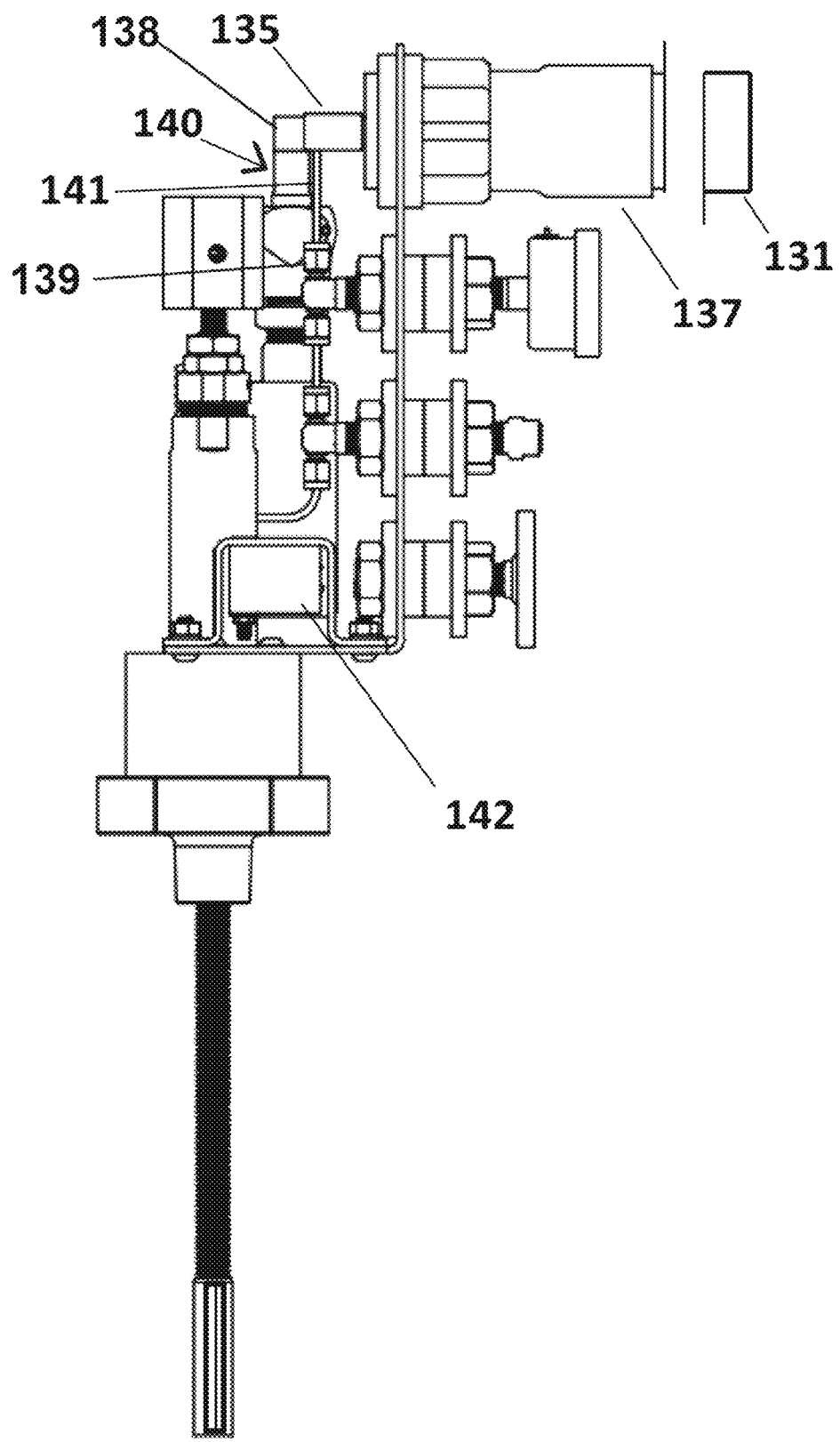
FIG. 18 is a side view of the invention of FIG. 17, illustrating the first end 131' of tube bundle 131 fully inserted and swaged in tube bundle boot 137, with power cord 136 engaging power cord receiver, and outlet tubing 141 engaging outlet tubing connection 139.

FIG. 17 illustrates the insertion of tube bundle 131 into tube bundle boot 137. FIG. 18 shows tube bundle 131 swaged into tube bundle boot 137. Heat trace with termination end 135 protrudes inside the modular sample system.

Power cord 136 is installed thru power cord receiver 138 and is connected to the wires of the electrically heated modular component 142 inside the conduit of power cord receiver 138.

The tube bundle sample tube 134 is connected to the outlet tubing connection 141.

Figure 19:
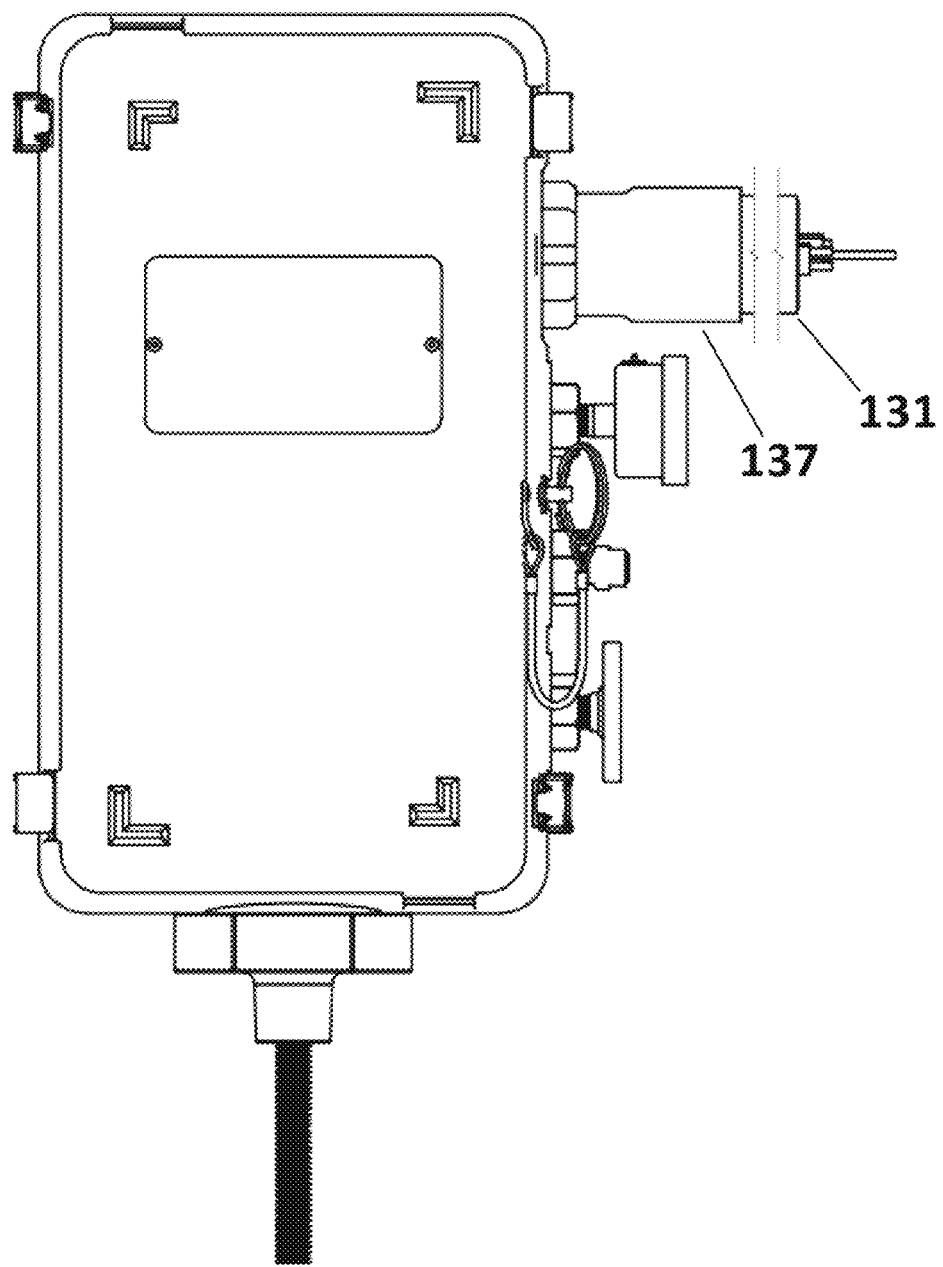
FIG. 19 is a side view of the invention of FIG. 18, illustrating the housing enclosing the modular conditioning system/bracket of the system of the present invention, with the tube bundle fully inserted into tube bundle boot 137, and power cord and outlet tubing integrated into the system.

FIG. 19 shows the modular sample system completed with the enclosure in place and the tube bundle with power cord installed.

The components in the present invention as shown are not intended to be limiting, as other components may be utilized in the present system with similar results. For example, another embodiment of the present invention could utilize the A+GENIE brand Membrane Separator with Liquid Block (as shown in U.S. Pat. No. 7,555,964, the contents of which are incorporated herein by reference thereto) just before the analyzer in a non-heated zone.

ELEMENTS OF THE INVENTION

P insertion probe
1 gas with entrained liquids
2 slotted probe tip
3 probe isolation valve
4 substrate coupling
5 modular sample conditioning system
6 regulator inlet
9 regulator
14 heat trace
15 bracket—modular sample conditioning system
16 enclosure
17 regulator base
20 probe passage
21 medial area of pipe/stream
22 regulator threaded fasteners
24 OD of probe
25, length, rack'
32,' outer surface, OD
33 heater cartridge housing
34 Inner diameter of heater cartridge
101 body
102,' insertion probe first, second ends
103,' first, second ends of body 101
104 outer wall
105 longitudinal axis
106 opening
107,' length, width
108 slot
109 O-Ring saddle (probe tip)
110 opening 106 ends
111,' first, second side walls
112,' outer, inner edges
113 outflow passage
114 threaded end of probe
115 ID outflow passage
116 capillary tube
117,' first, second ends
119 O-Ring retainer
120 receiver
121,' O-Ring,"
122 Probe lower end O-ring seal
127 flow component
128 back side of probe opposite slot opening
129,'," threaded apertures
130 solids filter screen
131,'," tube bundle, ends
132 tube bundle cover
133 tube bundle insulation
134 ⅛" OD stainless steel sample tube
135,' heat trace with end termination, heat trace
136 power cord included in tube bundle but separate from heat trace
137,',"  tube bundle boot, first, second ends
138 power cord receiver
139 outlet tubing connection
140 power cord connected to receiver
141 outlet tubing connected to tube bundle
142 electrically heated modular component
143 tube bundle length
144 inserted The invention embodiments herein described are done so in detail for exemplary purposes only, and may be subject to many different variations in design, structure, application and operation methodology. Thus, the detailed disclosures therein should be interpreted in an illustrative, exemplary manner, and not in a limited sense.

I claim:

1. A fluid sampling system for a wet gas fluid stream, comprising:
a sample probe consisting of a capillary flow path;
a modular conditioning component formed to receive flow from said sample probe via said capillary flow path, so as to provide a fluid sample;
a tube bundle;
a separate power cord within said tube bundle,
a tube bundle boot mounted to a bracket of a modular sample system,
said tube bundle formed to engage said tube bundle boot such that said power cord electrically engages a power cord receiver, so as to provide electricity to said modular conditioning component, so as to facilitate the processing of said fluid sample.

2. The method of claim 1, wherein said fluid sample comprises a multi-phase gas.

3. The method of claim 2, wherein said tube bundle boot comprises a power cord receiver for receiving and slidingly engaging said power cord so as to receive electricity therefrom.

4. The method of claim 1, wherein said sample probe utilizes said capillary flow path to facilitate capillary action in wet gas flowing therethrough, so as to prevent disassociation of said wet gas and provide a composite representative sample of said fluid stream.

5. The method of claim 4, wherein said tube bundle boot is formed to transfer power from said tube bundle to said modular conditioning component, heating same, providing a heated component; and wherein said heated component is formed to receive said composite representative sample.

6. The method of claim 5, wherein said heated component is formed to vaporize entrained liquids, providing a single-phase sample.

7. The method of claim 1, wherein said conditioning component comprises a heated pressure regulator.

8. The method of claim 1, wherein said conditioning component comprises a vaporizer.

9. The method of claim 1, wherein said sample probe comprises a linear slot.

10. The method of claim 9, wherein said sample probe comprises a conduit formed to receive flow from said linear slot.

11. The method of claim 10, wherein said linear slot and said conduit are sized to facilitate capillary action in wet gas flowing therethrough, so as to prevent disassociation of said wet gas flowing therethrough.

\* \* \* \* \*